(12) United States Patent
Patel et al.

(10) Patent No.: US 7,729,760 B2
(45) Date of Patent: Jun. 1, 2010

(54) PATIENT MANAGEMENT SYSTEM FOR PROVIDING PARAMETER DATA FOR AN IMPLANTABLE MEDICAL DEVICE

(75) Inventors: Sejal B. Patel, Pearland, TX (US); Jason D. Begnaud, Houston, TX (US); Chris G. DuPont, League City, TX (US); Albert A. Rodriguez, Friendswood, TX (US)

(73) Assignee: Cyberonics, Inc., Houston, TX (US)

( * ) Notice: Subject to any disclaimer, the term of this patent is extended or adjusted under 35 U.S.C. 154(b) by 653 days.

(21) Appl. No.: 11/588,700

(22) Filed: Oct. 27, 2006

(65) Prior Publication Data

US 2008/0103533 A1    May 1, 2008

(51) Int. Cl.
*A61N 1/00* (2006.01)
(52) U.S. Cl. .......................................................... 607/2
(58) Field of Classification Search ................... 607/60, 607/45, 2
See application file for complete search history.

(56) References Cited

U.S. PATENT DOCUMENTS

2006/0015153 A1    1/2006  Gliner et al. .................. 607/45
2006/0149337 A1*  7/2006  John ............................. 607/45
2006/0241725 A1* 10/2006  Libbus et al. ................. 607/60

FOREIGN PATENT DOCUMENTS

WO    WO2004/036372    4/2004

\* cited by examiner

*Primary Examiner*—George Manuel
*Assistant Examiner*—Robert N Wieland
(74) *Attorney, Agent, or Firm*—Williams, Morgan & Amerson, P.C.; Timothy L. Scott

(57) ABSTRACT

A method, system, graphical user interface, and apparatus are provided for performing a patient management function providing parameter data for delivering a therapeutic signal. A first electrical signal comprising a first therapy parameter is applied to a portion of a patient's body for providing a therapy. At least one patient parameter relating to an effect of applying the first electrical signal is acquired. A second therapy parameter for defining a second electrical signal to provide a therapy is determined in response to the patient parameter. The second therapy parameter is displayed on an external device. An input signal for defining the second electrical signal is received. The input signal includes a signal indicative of the whether the second therapy parameter was accepted or not.

23 Claims, 11 Drawing Sheets

PATIENT MANAGEMENT SYSTEM FOR PROVIDING PARAMETER DATA FOR AN IMPLANTABLE MEDICAL DEVICE

BACKGROUND OF THE INVENTION

1. Field of the Invention

This invention relates generally to implantable medical device systems and, more particularly, a patient management system to provide an interactive forum for managing patient care, the patient management system to also provide parameter data for treating one or more disorders using an implantable medical device (IMD).

2. Description of the Related Art

Many advancements have been made in treating diseases such as epilepsy. Therapies using electrical signals for treating these diseases have been found to effective. Implantable medical devices have been effectively used to deliver therapeutic stimulation to various portions of the human body (e.g., the vagus nerve) for treating these diseases. As used herein, "stimulation" or "stimulation signal" refers to the application of an electrical, mechanical, magnetic, electromagnetic, photonic, audio and/or chemical signal to a neural structure in the patient's body. The signal is an exogenous signal that is distinct from the endogenous electrical, mechanical, and chemical activity (e.g., afferent and/or efferent electrical action potentials) generated by the patient's body and environment. In other words, the stimulation signal (whether electrical, mechanical, magnetic, electro-magnetic, photonic, audio or chemical in nature) applied to the nerve in the present invention is a signal applied from an artificial source, e.g., a neurostimulator.

A "therapeutic signal" refers to a stimulation signal delivered to a patient's body with the intent of treating a disorder by providing a modulating effect to neural tissue. The effect of a stimulation signal on neuronal activity is termed "modulation"; however, for simplicity, the terms "stimulating" and "modulating", and variants thereof, are sometimes used interchangeably herein. In general, however, the delivery of an exogenous signal itself refers to "stimulation" of the neural structure, while the effects of that signal, if any, on the electrical activity of the neural structure are properly referred to as "modulation." The modulating effect of the stimulation signal upon the neural tissue may be excitatory or inhibitory, and may potentiate acute and/or long-term changes in neuronal activity. For example, the "modulating" effect of the stimulation signal to the neural tissue may comprise one more of the following effects: (a) initiation of an action potential (afferent, and/or efferent action potentials); (b) inhibition or blocking of the conduction of action potentials, whether endogenous or exogenously induced, including hyperpolarizing and/or collision blocking, (c) affecting changes in neurotransmitter/neuromodulator release or uptake, and (d) changes in neuro-plasticity or neurogenesis of brain tissue.

Electrical neurostimulation may be provided by implanting an electrical device underneath the skin of a patient and delivering an electrical signal to a nerve such as a cranial nerve. In one embodiment, the electrical neurostimulation involves sensing or detecting a body parameter, with the electrical signal being delivered in response to the sensed body parameter. This type of stimulation is generally referred to as "active," "feedback," or "triggered" stimulation. In another embodiment, the system may operate without sensing or detecting a body parameter once the patient has been diagnosed with a medical condition that may be treated by neurostimulation. In this case, the system may apply a series of electrical pulses to the nerve (e.g., a cranial nerve such as a vagus nerve) periodically, intermittently, or continuously throughout the day, or over another predetermined time interval. This type of stimulation is generally referred to as "passive," "non-feedback," or "prophylactic," stimulation. The electrical signal may be applied by an IMD that is implanted within the patient's body. In another alternative embodiment, the signal may be generated by an external pulse generator outside the patient's body, coupled by an RF or wireless link to an implanted electrode.

Generally, neurostimulation signals that perform neuromodulation are delivered by the implantable medical device via one or more leads. The leads generally terminate at their distal ends in one or more electrodes, and the electrodes in turn are electrically coupled to a tissue in the patient's body. For example, a number of electrodes may be attached to various points of a nerve or other tissue inside a human body for delivery of a neurostimulation signal.

State-of-the-art implantable medical systems utilize an external device to communicate with the IMD for programming the therapeutical electrical signal to be delivered by the implanted device, performing diagnostics and making adjustments to one or more parameters defining the therapeutic electrical signal. A physician may assess the progress of a particular therapy regimen given to a patient during office visits. The physician may examine the patient and make a determination as to the efficacy of the therapy being delivered and may use the external device to reprogram or adjust various stimulation parameters that will modify subsequent therapy delivered to the patient.

There are various problems associated with state-of-the-art implanted neurostimulators. For example, one problem with state-of-the-art implanted neurostimulators is the fact that tedious record-keeping and study of charts are required to perform therapy management to treat patients. When the physician evaluates a patient, various settings for therapy delivered by the IMD are documented in the patient's chart at each visit. At subsequent visits, the physician may then examine previous entries into the chart (e.g., the physician may study the various parameters defining the therapeutic electrical signal, medications taken by the patient, etc.) to make adjustments to the therapy delivered by the IMD. The process of documenting the changes in the parameters, medication and patient evaluation may become quite tedious as well as time-consuming, with a corresponding risk that important information may not be collected or may not be incorporated into the adjustments made to the therapy to improve or maintain efficacy. Further, examining all of the previous chart entries along with the current patient evaluation to determine an appropriate therapy for the patient may become cumbersome or unfeasible, especially where large volumes of data must be collected and correlated. Further, inherent changes or other trends (e.g., progressive changes in a disease symptom) may not be easily detected by the physician upon a review of the various entries in the patient's chart. Therefore, opportunities to improve the efficacy of the therapy may be inadvertently missed due to the tedious nature of patient evaluation and the voluminous data entries made to a patient's chart, as well as to insufficient or improper evaluation of the data collected.

Another problem associated with state-of-the-art IMD systems is the fact that there is a requirement that users (e.g., physicians) independently select various therapy parameters, such as output current and pulse-width, etc., and monitor the effects of the therapy for a particular patient over a period of time. This study of efficacy may reveal some therapy-response data relating to a particular patient. State-of-the-art databases associated with IMD systems generally store data relating to parameters associated with a particular patient in a patient-by-patient basis. However, the industry generally lacks an efficient cross-patient correlation technique to show meaningful relationship between therapy parameters and therapeutic efficacy. Utilizing the data relating to parameters associated with the patient-by-patient analysis described above, physicians must determine various parameters that may be effective for a particular patient. However, one problem associated with this technique is the fact that a set of parameters that is effective for one patient may not be ideal for another patient. The state-of-the-art generally lacks a method of performing an evaluation of favorable therapy parameters that may be employed for a particular type of patient. This may prompt the requirement of several iterations in a trial-and-error type of estimation process for determining appropriate parameters for achieving desirable efficacy and results when treating a patient.

The present invention is directed to overcoming, or at least reducing, the effects of one or more of the problems set forth above.

SUMMARY OF THE INVENTION

In one aspect, the present invention provides a method for performing a patient management function for providing parameter data to define a therapeutic electrical signal. A first electrical signal comprising a first therapy parameter is applied to a portion of a patient's body for providing a first therapy. At least one patient parameter relating to an effect of applying the first electrical signal is acquired. A second therapy parameter for defining a second electrical signal to provide a second therapy is determined in response to the patient parameter. The second therapy parameter is displayed on an external device. An input signal for defining the second electrical signal is received. The input signal includes a signal indicative of the selection of the second therapy parameter, a signal indicative of not selecting the second therapy parameter, and/or a signal indicative of a third therapy parameter.

In another aspect, the present invention provides a method for performing a patient management function for providing parameter data to define a therapeutic electrical signal. A plurality of values relating to at least one patient parameter associated with a first electrical signal applied to a patient's body to provide a first therapy is acquired. The first electrical signal includes a first therapy parameter. An efficacy factor is determined based upon the patient parameter. Determining the efficacy factor includes analyzing a trend associated with the plurality of values relating to the at least one patient parameter. A second therapy parameter is determined based upon the efficacy factor. The second therapy parameter is displayed. An input signal for defining the second electrical signal is received. The input signal includes a signal indicative of the selection of the second therapy parameter, a signal indicative of not selecting the second therapy parameter, and/or a signal indicative of a third therapy parameter.

In another aspect, the present invention provides a method for performing a patient management function for providing parameter data for defining a therapeutic electrical signal. Data indicative of a first patient parameter is acquired for a plurality of patients following the application of a therapeutic electrical signal to a vagus nerve of each of said patients. The electrical signal includes a first therapy parameter. A statistical relationship between the data indicative of the first patient parameter and the first therapy parameter is determined. The statistical relationship is displayed. An input signal for defining an electrical signal for a patient based upon the statistical relationship is received.

In yet another aspect, the present invention provides a method for performing a patient management function for providing parameter data for defining a therapeutic electrical signal. An input signal indicative of a desired patient parameter that would be responsive to a therapeutic electrical signal applied to the vagus nerve of a patient is received. At least one recommended therapy parameter defining the electrical signal for achieving the desired patient parameter is determined. The recommended therapy parameter is displayed. An input signal for defining the electrical signal based upon the recommended therapy parameter is received.

In another aspect, a graphical user interface integrated into an external device is provided for performing a patient management function for providing parameter data for delivering a therapeutic electrical signal using an implanted medical device. The graphical user interface includes a first display region adapted to display a visual indication of a graphical representation of a second therapy parameter. The second therapy parameter is based upon a patient parameter relating to an effect of applying a first electrical signal comprising a first therapy parameter to a vagus nerve of a patient. The graphical user interface also includes a second display region for receiving an input signal for defining a second electrical signal. The input signal for defining the second electrical signal includes a signal indicative of the selection of the second therapy parameter, a signal indicative of not selected the second therapy parameter, and/or a signal indicative of a third therapy parameter In yet another aspect of the present invention, a computer readable program storage device encoded with instructions is provided for performing a patient management function for providing parameter data for defining a therapeutic electrical signal. The computer readable program storage device is encoded with instructions that, when executed by a computer, performs a method, which comprises: applying a first electrical signal comprising a first therapy parameter to a vagus nerve of a patient; acquiring at least one patient parameter relating to an effect of applying the first electrical signal to the vagus nerve of the patient; determining a second therapy parameter for defining a second electrical signal to provide a therapy in response to the patient parameter; displaying the second therapy parameter on an external device; and receiving an input signal for defining the second electrical signal. The input signal includes a signal indicative of the selection of the second therapy parameter, signal indicative of not selecting the second therapy parameter, and/or a signal indicative of a third therapy parameter.

BRIEF DESCRIPTION OF THE DRAWINGS

The invention may be understood by reference to the following description taken in conjunction with the accompanying drawings, in which like reference numerals identify like elements, and in which.

DETAILED DESCRIPTION OF SPECIFIC EMBODIMENTS

Figure 1:
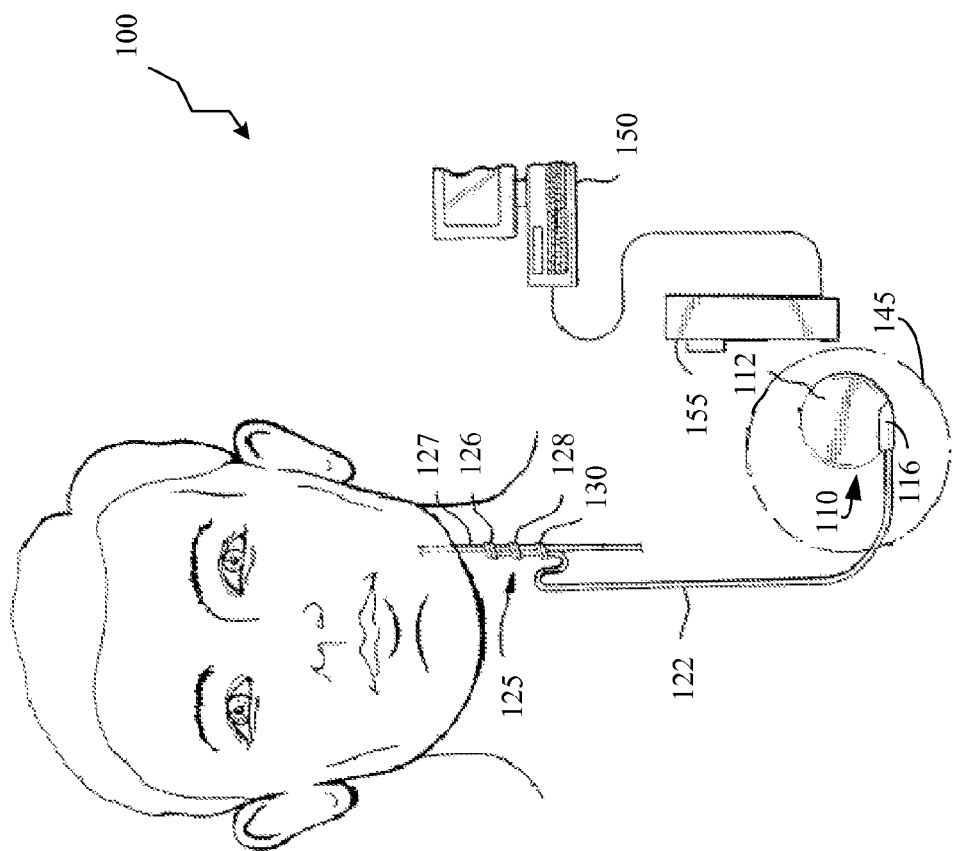
FIG. 1 provides a stylized diagram of an implantable medical device implanted into a patient's body for providing a therapeutic electrical signal to a neural structure of the patient's body, in accordance with one illustrative embodiment of the present invention.

Illustrative embodiments of the invention are described herein. In the interest of clarity, not all features of an actual implementation are described in this specification. In the development of any such actual embodiment, numerous implementation-specific decisions must be made to achieve the design-specific goals, which will vary from one implementation to another. It will be appreciated that such a development effort, while possibly complex and time-consuming, would nevertheless be a routine undertaking for persons of ordinary skill in the art having the benefit of this disclosure.

This document does not intend to distinguish between components that differ in name but not function. In the following discussion and in the claims, the terms "including" and "includes" are used in an open-ended fashion, and thus should be interpreted to mean "including, but not limited to." Also, the term "couple" or "couples" is intended to mean either a direct or an indirect electrical connection. "Direct contact," "direct attachment," or providing a "direct coupling" indicates that a surface of a first element contacts the surface of a second element with no substantial attenuating medium therebetween. The presence of substances, such as bodily fluids, that do not substantially attenuate electrical connections does not vitiate direct contact. The word "or" is used in the inclusive sense (i.e., "and/or") unless a specific use to the contrary is explicitly stated.

The term "electrode" or "electrodes" described herein may refer to one or more stimulation electrodes (i.e., electrodes for delivering an electrical signal generated by an IMD to a tissue), sensing electrodes (i.e., electrodes for sensing a physiological indication of a patient's body), and/or electrodes that are capable of delivering a stimulation signal, as well as performing a sensing function.

Cranial nerve stimulation has been proposed to treat a number of nervous system disorders, including epilepsy and other movement disorders, depression, anxiety disorders and other neuropsychiatric disorders, dementia, head trauma, coma, migraine headache, obesity, eating disorders, sleep disorders, cardiac disorders (such as congestive heart failure and atrial fibrillation), hypertension, endocrine disorders (such as diabetes and hypoglycemia), and pain, among others. See, e.g., U.S. Pats. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the numerous disorders for which cranial nerve stimulation has been proposed or suggested as a treatment option, the fact that detailed neural pathways for many (if not all) cranial nerves remain relatively unknown, makes predictions of efficacy for any given disorder difficult or impossible. Moreover, even if such pathways were known, moreover, the precise stimulation parameters that would modulate particular pathways relevant to a particular disorder generally cannot be predicted.

Despite the difficulties of predicting efficacy for particular disorders, the use of vagus nerve stimulation as a therapy for treating epilepsy and/or depression is an established therapy option. Although many patients respond well to the therapy, a significant number of patients must have the therapeutic electrical signal adjusted periodically to cause and/or maintain a positive therapeutic response. The present invention provides a patient management system for capturing and incorporating into the therapy decision-making process, information relevant to the patient's condition and course of treatment. More specifically, embodiments of the present invention provide for a patient management system for automated documentation and evaluation of various patient parameters and therapy parameters relating to an operation of an IMD system for treating a medical condition such as epilepsy or depression. The patient management system provided by embodiments of the present invention facilitates the processes of documentation and analysis of various patient and electrical signal parameters associated with a medical condition such as epilepsy or depression. This documentation process may be useful in identifying various trends relating to treatment efficacy. Using this data, a physician may determine whether changes in therapy and/or medication would be desirable to maintain and/or improve efficacy for a particular patient.

The patient management system of the present invention provides for a software module that is capable of acquiring, storing, and processing various forms of data, such as patient data/parameters (e.g., physiological data, side-effect data such as effects on heart rate and breathing, brain-activity parameters, disease progression or regression data, self-evaluation data, seizure characteristic data, quality of life data, etc.) and therapy parameter data. Therapy parameters may include, but are not limited to, electrical signal parameters that define the therapeutic electrical signals delivered by the IMD, medication parameters (e.g., dosages, frequency of medication provided to the patient, etc), and/or any other therapeutic treatment parameter. In an alternative embodiment, the term "therapy parameters" may refer to electrical signal parameters defining the therapeutic electrical signals delivered by the IMD. Therapy parameters for a therapeutic electrical signal may also include, but are not limited to, a current amplitude, a voltage amplitude, a rate of change of said current amplitude, a rate of change of said voltage amplitude, a time period of a rate of change of said current amplitude, a time period of a rate of change of said voltage amplitude, a pulse width, a rate of change of the pulse width, a time period of a rate of change of the pulse width, a frequency, a rate of change of the frequency, a time period of a rate of change of the frequency, a signal on-time, a signal off-time, and/or a duty cycle.

Other diagnostics and physician interaction data may also be stored by the patient management system of the present invention. For example, the patient management system may provide for storage of the date of a patient's visit to a physician, changes made to various parameters associated with the IMD and the dates of such changes, physician inputs, patient inputs, etc.

In one embodiment, the patient management system of the present invention also provides for a graphical user interface (GUI) that may be interactive. The GUI of the patient management system may facilitate the entry of various physician inputs, such as the selection of a mode of operation for the patient management system. Once a certain mode, such as an input mode, evaluation mode, therapy adjustment mode, etc., is initiated by a user (e.g., a physician, a nurse, or a medical technician), the patient management system may provide for an interactive interface to acquire, process, store, and/or display various data associated with a therapeutic electrical signal delivered to a patient. The patient management system may store this information and provide a trend-type information display using the GUI. For example, by analyzing the information relating to various seizure parameter(s), quality of life input, etc., along with therapy parameters over time, a physician for an epilepsy patient may then evaluate the progress of therapy and make appropriate adjustments. Similar analyses may be performed for other medical conditions such as depression. Various therapy settings, medication levels, etc., may be adjusted to improve the efficacy of the therapy and the patient's quality of life.

Embodiments of the present invention provide for a patient management function capable of providing guidance for selecting various therapy parameters for delivering a therapeutic electrical signal using an implantable medical device (e.g., a neurostimulation device). The patient management system of the present invention provides for determining a set of therapy parameters based upon analyses of efficacy data relating to treatment history of a particular patient, a group of pre-selected patients, a group of randomly selected patients, and/or data relating to a history of all patients that were treated using an IMD. A database may be used to store therapy parameters and various patient parameters. This database may be used by a patient management system of an embodiment of the present invention to calculate or determine one or more recommended therapy parameters to obtain a predetermined level of efficacy.

Embodiments of the present invention may provide for receiving data from a user/physician to assess the type of efficacy and results that are desired in light of a patient's tolerance and/or other patient parameters, and determine various therapy parameters that may be accepted by the user to perform the therapy. Further, data relating to a large number of patients may be analyzed to perform a statistical analysis of results versus the type of therapy parameters that were employed. A correlation between a range of therapy parameter values may then be processed to suggest various therapy parameters to achieve the objectives indicated by the user. The patient management system of the present invention may be capable of automated documentation and evaluation of various patient parameters and therapy parameters relating to an operation of an IMD system.

Although not so limited, a system capable of implementing embodiments of the present invention is described below. FIG. 1 depicts a stylized implantable medical system 100 for implementing one or more embodiments of the present invention. An electrical signal generator 110 is provided, having a main body 112 comprising a case or shell with a header 116 for connecting to an insulated, electrically conductive lead assembly 122. The generator 110 is implanted in the patient's chest in a pocket or cavity formed by the implanting surgeon just below the skin (indicated by a dotted line 145, similar to the implantation procedure for a pacemaker pulse generator.

A nerve electrode assembly 125, preferably comprising a plurality of electrodes having at least an electrode pair, is conductively connected to the distal end of the lead assembly 122, which preferably comprises a plurality of lead wires (one wire for each electrode). Each electrode in the electrode assembly 125 may operate independently or alternatively, may operate in conjunction with the other electrodes.

Lead assembly 122 is attached at its proximal end to connectors on the header 116 of generator 110. The electrode assembly 125 may be surgically coupled to a vagus nerve 127 in the patient's neck or at another location, e.g., near the patient's diaphragm. Other (or additional) cranial nerves may also be used to deliver the electrical signal. In one embodiment, the electrode assembly 125 comprises a bipolar stimulating electrode pair 126, 128. Suitable electrode assemblies are available from Cyberonics, Inc., Houston, Tex., USA as the Model 302 electrode assembly. However, persons of skill in the art will appreciate that many electrode designs could be used in the present invention. In one embodiment, the two electrodes are wrapped about the vagus nerve, and the electrode assembly 125 may be secured to the nerve 127 by a spiral anchoring tether 130 such as that disclosed in U.S. Pat. No. 4,979,511 issued Dec. 25, 1990 to Reese S. Terry, Jr. and assigned to the same assignee as the instant application. Lead assembly 122 is secured, while retaining the ability to flex with movement of the chest and neck, by a suture connection to nearby tissue (not shown).

In alternative embodiments, the electrode assembly 125 may comprise temperature sensing elements and/or heart rate sensor elements. Other sensors for other body parameters may also be employed to trigger active stimulation. Both passive and active stimulation may be combined or delivered by a single IMD according to the present invention. Either or both modes may be appropriate to treat a specific patient under observation.

The electrical pulse generator 110 may be programmed with an external computer 150 using programming software based on the description herein. A programming wand 155 may be used to facilitate radio frequency (RF) communication between the computer 150 and the pulse generator 110. The programming wand 155 and computer 150 permit non-invasive communication with the generator 110 after the latter is implanted. In systems where the computer 150 uses one or more channels in the Medical Implant Communications Service (MICS) bandwidths, the programming wand 155 may be omitted to permit more convenient communication directly between the computer 150 and the pulse generator 110.

Figure 2A:
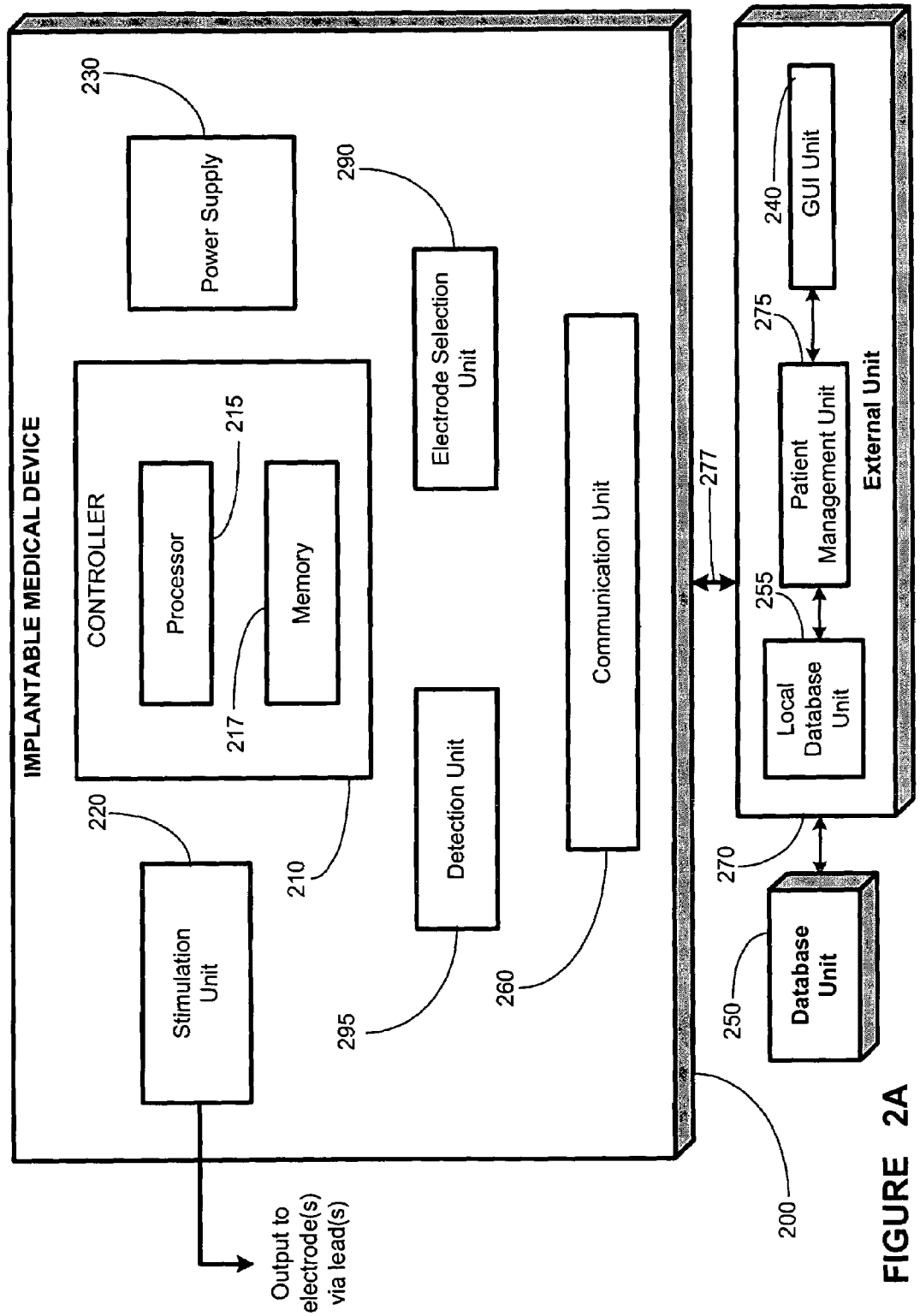
FIG. 2A is a block diagram of a medical device system that includes an implantable medical device and an external device that includes a graphical user interface unit for providing a patient management system for the implantable medical device, in accordance with one illustrative embodiment of the present invention.

Turning now to FIG. 2A, a block diagram depiction of the IMD 200 is provided, in accordance with an illustrative embodiment of the present invention. The IMD 200 (such as generator 110 from FIG. 1) may comprise a controller 210 capable of controlling various aspects of the operation of the IMD 200. The controller 210 is capable of receiving internal data or external data and causing a stimulation unit 220 to generate and deliver an electrical signal to target tissues of the patient's body for treating a medical condition. For example, the controller 210 may receive manual instructions from an operator externally, or may cause the electrical signal to be generated and delivered based on internal calculations and programming. The controller 210 is capable of affecting substantially all functions of the IMD 200.

The controller 210 may comprise various components, such as a processor 215, a memory 217, etc. The processor 215 may comprise one or more microcontrollers, microprocessors, etc., capable of performing various executions of software components. The memory 217 may comprise various memory portions where a number of types of data (e.g., internal data, external data instructions, software codes, status data, diagnostic data, etc.) may be stored. The memory 217 may comprise one or more of random access memory (RAM) dynamic random access memory (DRAM), electrically erasable programmable read-only memory (EEPROM), flash memory, etc.

The IMD 200 may also comprise a stimulation unit 220 capable of generating and delivering electrical signals to one or more electrodes via leads. A lead assembly 122 may be coupled to the IMD 200. Therapy may be delivered to the leads comprising the lead assembly 122 by the stimulation unit 220 based upon instructions from the controller 210. The stimulation unit 220 may comprise various circuitry, such as stimulation signal generators, impedance control circuitry to control the impedance "seen" by the leads, and other circuitry that receives instructions relating to the delivery of the electrical signal to tissue. The stimulation unit 220 is capable of delivering a controlled current electrical signal over the leads comprising the lead assembly 122.

The IMD 200 may also comprise a power supply 230. The power supply 230 may comprise a battery, voltage regulators, capacitors, etc., to provide power for the operation of the IMD 200, including delivering the therapeutic electrical signal. The power supply 230 comprises a power source that in some embodiments may be rechargeable. In other embodiments, a non-rechargeable power source may be used. The power supply 230 provides power for the operation of the IMD 200, including electronic operations and the electrical signal generation and delivery functions. The power supply 230 may comprise a lithium/thionyl chloride cell or a lithium/carbon monofluoride (LiCFx) cell. Other battery types known in the art of implantable medical devices may also be used.

The IMD 200 may also comprise a communication unit 260 capable of facilitating communications between the IMD 200 and various devices. In particular, the communication unit 260 is capable of providing transmission and reception of electronic signals to and from an external unit 270, such as computer 150 and wand 155 (FIG. 1). The communication unit 260 may include hardware, software, firmware, or any combination thereof.

The external unit 270 may be a device that is capable of programming various modules and electrical signal parameters of the IMD 200. In one embodiment, the external unit 270 is a computer system capable of executing a data-acquisition program. The external unit 270 may be controlled by a healthcare provider, such as a physician, at a base station in, for example, a doctor's office. In alternative embodiments, the external unit 270 may be controlled by a patient in a system providing less control over the operation of the IMD 200 than another external unit 270 controlled by a healthcare provider. Whether controlled by the patient or by a healthcare provider, the external unit 270 may be a computer, preferably a handheld computer or PDA, but may alternatively comprise any other device that is capable of electronic communications and programming, e.g., hand-held computer system, a PC computer system, a laptop computer system, a server, a personal digital assistant (PDA), and an Apple-based computer system. The external unit 270 may download various parameters and program software into the IMD 200 for programming the operation of the IMD, and may also receive and upload various status conditions and other data from the IMD 200. Communications between the external unit 270 and the communication unit 260 in the IMD 200 may occur via a wireless or other type of communication, represented generally by line 277 in FIGS. 2A and 2B. This may occur using, e.g., wand 155 (FIG. 1) to communicate by RF energy with a generator 110. Alternatively, the wand may be omitted in some systems, e.g., systems in which external unit 270 operates in the MICS bandwidths.

The IMD 200 also comprises a detection unit 295 that is capable of detecting various patient parameters. For example, the detection unit 295 may comprise hardware, software, or firmware that are capable of determining data relating to one or more body parameters of the patient relevant to the patient's disorder, e.g., epilepsy or depression. Based upon the data deciphered by the detection unit 295, the IMD 200 may deliver the electrical signal to a portion of the vagus nerve to treat epilepsy. In one embodiment, the detection unit 295 may be capable of detecting a feedback response from the patient. The feedback response may include a magnetic signal input, a tap input, a wireless data input to the IMD 200, etc. The feedback may be indicative of a pain and/or noxious threshold, wherein the threshold may be the limit of tolerance of discomfort for a particular patient. The term "patient parameters" may refer to, but is not limited to, various body parameters, which may in some embodiments involve sensors coupled to the IMD 200. The patient parameters may include quality of life indication(s), seizure frequency parameter(s), seizure characteristic parameter(s), side effect parameter(s), a brain-activity parameter(s), depression score parameters, and/or medication dosage parameter(s), etc.

The IMD 200 may also comprise an electrode selection unit 290 that is capable of directing an electrical signal to one or more of a plurality of electrodes that are operationally coupled to various portions of the vagus nerve. The electrode selection unit 290 may direct a stimulation signal to the left vagus main trunk, the right vagus main trunk, or a branch of the left or right vagus nerves, or may "steer" the electrical signal to particular nerve axons within the main vagus nerve trunk by selected particular electrodes from among a plurality of electrodes coupled to portions of the vagus nerve. In this way, the stimulation target unit is capable of targeting a predetermined portion of the vagus nerve. Therefore, based upon a particular type of data detected by the detection unit 295, the electrode selection unit 290 may provide a signal capable of generating afferent action potentials, efferent action potentials, blocking afferent and/or efferent action potentials, or a combination of the foregoing effects to treat epilepsy.

The external unit 270 may comprise a patient management unit 275 that is capable of performing the various patient management processes described herein. The patient management unit 275 is capable of performing various diagnostics of the IMD 200, as well as acquiring, storing and/or processing data relating to the therapy delivered by the IMD 200. The patient management unit 275 is capable of providing guidance for selecting therapy parameters. The patient management unit 275 is capable of utilizing a collection of efficacy data for a particular patient or a group of patients. The patient management unit 275 may perform statistical analysis to construct necessary statistical breakdowns of a larger population of patients, along with parameters associated those patients. Various information resulting from this analysis may be provided in a text or in a graphical format. Display of the overall data relating to the analysis of various patient data may be provided to a user, wherein the user may compare a particular patient's efficacy and therapy parameters to those of a number of patients. In this manner, a user may determine which therapy parameters are effective for most patients in achieving a particular therapy result. More detailed description of the patient management unit 270 is provided in FIG. 4 and the accompanying description below.

In one embodiment, external unit 270 comprises a graphical user interface (GUI) unit 240. It will be appreciated that GUI unit 240 may also be a separate unit from external unit 270. Regardless of whether the GUI unit 240 is part of, or separate from, external unit 270, the external unit 270 is capable of driving various displays on the GUI unit 240. In one embodiment, the GUI unit 240 is capable not only of receiving data from the external unit 270 for driving one or more displays, but also of receiving inputs from a user, such as a physician or patient, and transmitting the data to the patient management unit 275. The GUI unit 240 may be comprised of a variety of devices, including, but not limited to, a computer terminal, a cathode ray tube (CRT) device, a liquid crystal device (LCD) module, a plasma-display device, etc. The GUI unit 240 may include a touch sensitive screen monitor that is capable of detecting an external input from the user. It may also be a handheld device, such as a personal digital assistant (PDA), a pen input device, a portable computer device, etc.

In one embodiment, the external unit 270 may comprise a local database unit 255 from which the patient management unit 275 may receive data. Optionally or alternatively, the external unit 270 may also be coupled to a database unit 250, which may be separate from external unit 270 (e.g., a centralized database wirelessly linked to a handheld external unit 270). The database unit 250 and/or the local database unit 255 are capable of storing various patient data. This data may comprise patient parameter data acquired from a patient's body and/or therapy parameter data. The database unit 250 and/or the local database unit 255 may comprise data for a plurality of patients, and may be organized and stored in a variety of manners, such as in date format, severity of disease format, etc. The database unit 250 and/or the local database unit 255 may be relational databases in one embodiment. A physician may perform various patient management functions described below using the GUI unit 240, which may display data from the IMD 200 and/or data from the database unit 250 and/or the local database unit 255. The database unit 250 and/or the local database unit 255 may store various patient data such as seizure types, etc. Inputs into the GUI unit 240 may be sent to the IMD 200 to modify various parameters for the therapeutic electrical signal.

One or more of the blocks illustrated in the block diagram of IMD 200, in FIG. 2A, may comprise hardware units, software units, firmware units or any combination thereof. Additionally, one or more blocks illustrated in FIG. 2A may be combined with other blocks, which may represent circuit hardware units, software algorithms, etc. Additionally, any number of the circuitry or software units associated with the various blocks illustrated in FIG. 2A may be combined into a programmable device, such as a field programmable gate array, an ASIC device, etc.

Figure 2B:
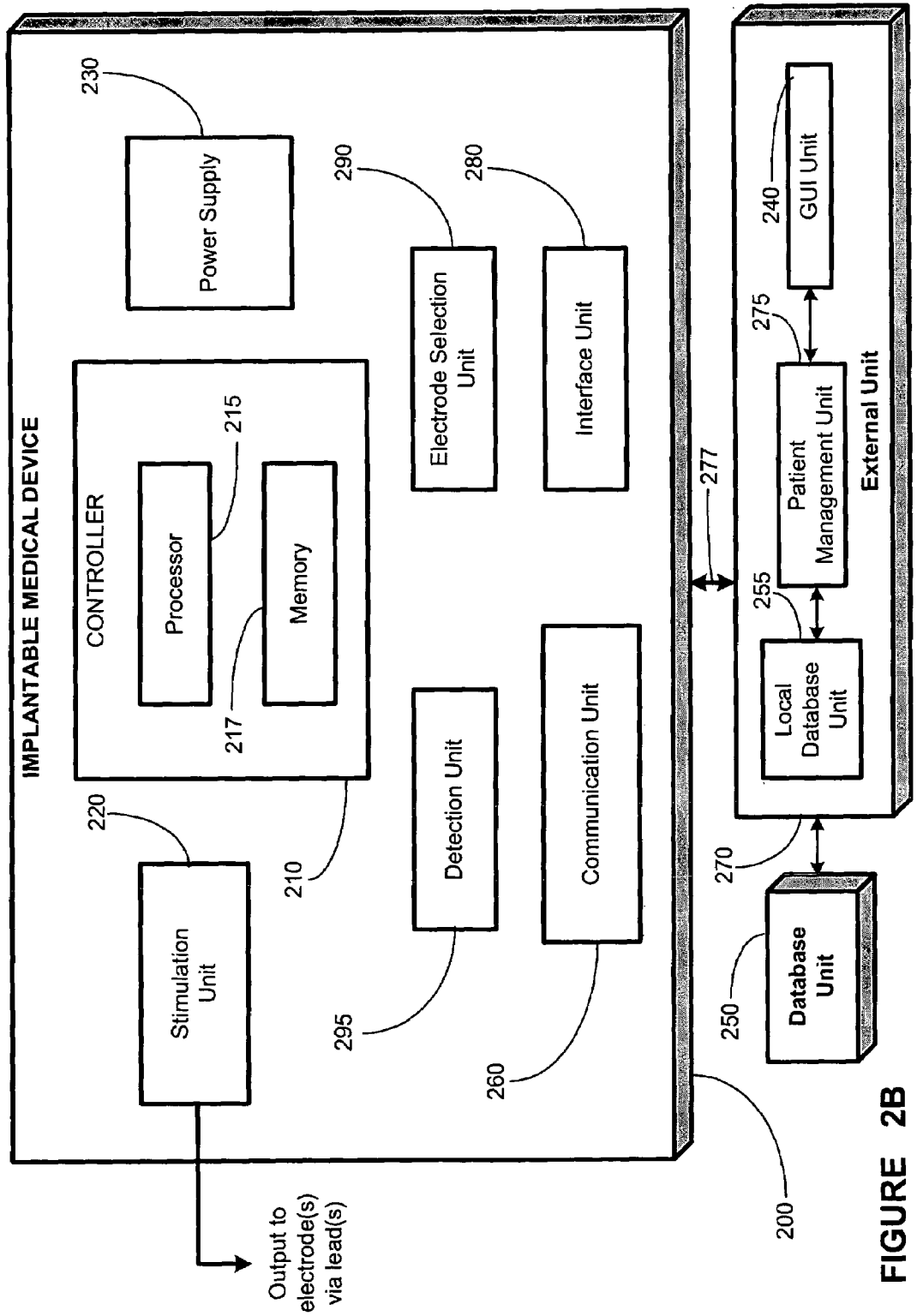
FIG. 2B is a block diagram of a medical device system that includes an implantable medical device and an external device that includes a graphical user interface unit for providing a patient management system for the implantable medical device, in accordance with an alternative illustrative embodiment of the present invention.

Turning now to FIG. 2B, a block diagram depiction of the IMD 200 is provided, in accordance with an alternative illustrative embodiment of the present invention. The various blocks of FIG. 2B that correspond to similar blocks of FIG. 2A operate in a similar fashion. Additionally, the alternative embodiment of FIG. 2B also comprises an interface unit 280. The interface unit 280 is capable of communications with the external unit 270. The interface unit 280 may receive instructions and/or data from the external unit 270 via the communication unit 260. The interface unit 280 is capable of various tasks, such as accessing the memory 217 in the IMD 200. Further, the interface unit 280 is capable of providing requested data to the external unit 270 to be displayed by the external unit 270. More detailed description of the interface unit 280 is provided in FIG. 3 and the accompanying description below.

Figure 3:
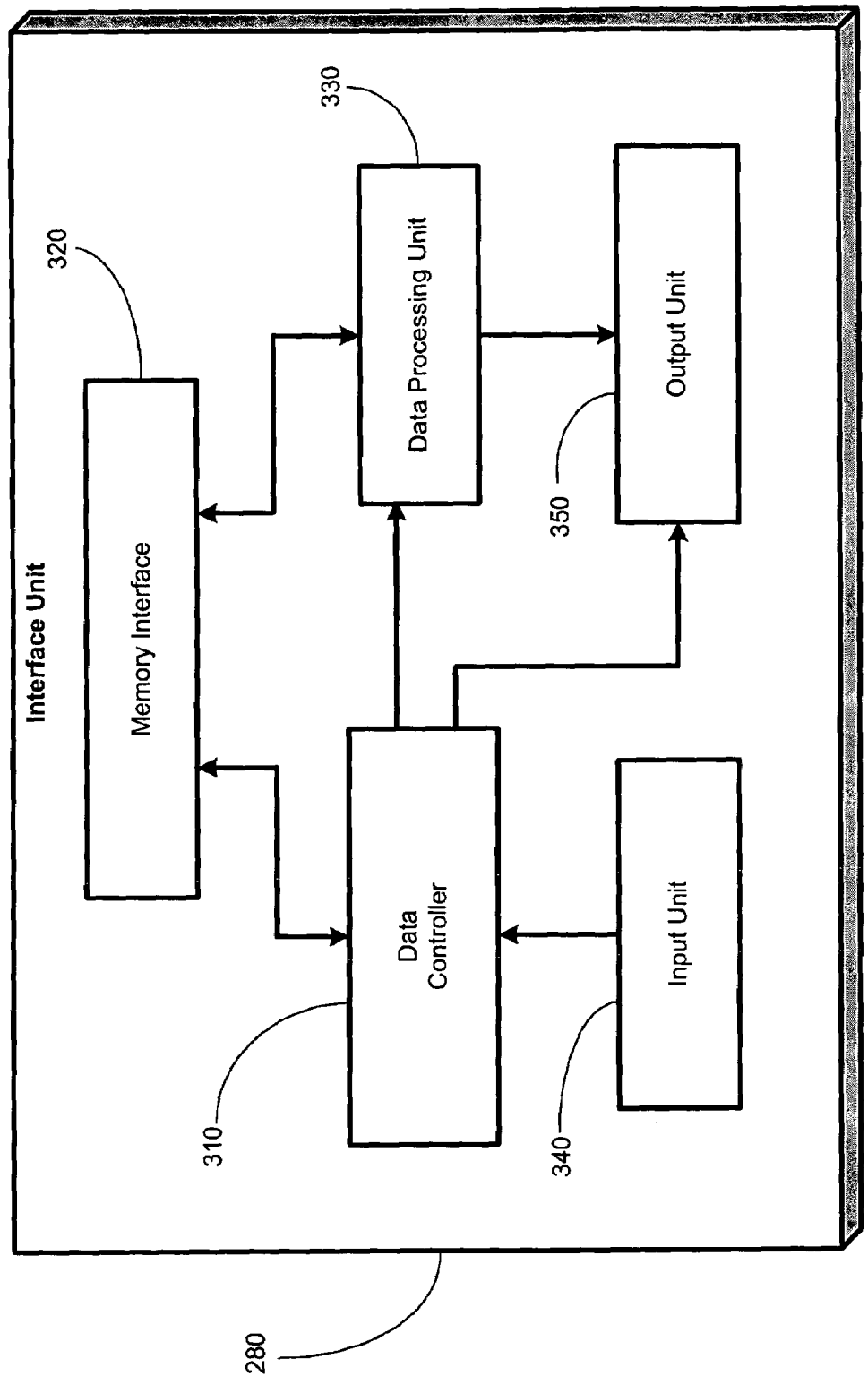
FIG. 3 is a more detailed block diagram of the interface unit of FIG. 2B, in accordance with one illustrative embodiment of the present invention.

Turning now to FIG. 3, a more detailed block diagram depiction of the interface unit 280 of FIG. 2B, in accordance with one illustrative embodiment of the present invention, is provided. The interface unit 280 may comprise a memory interface 320 that is capable of receiving data from, and/or storing data into the memory 217 of the IMD 200. The memory interface 320 may comprise various hardware and/or firmware objects to facilitate access to the memory 217.

The interface unit 280 also comprises a data controller 310. The data controller 310 is capable of controlling the various functions performed by the interface unit 280, such as receiving and processing information from the external unit 270, as well as providing various parametric data to various portions of the IMD 200. The interface unit 280 may also comprise a data processing unit 330. The data processing unit 330 is capable of processing various patient parameter data and stimulation-related data. For example, upon a command from the external unit 270, the data processing unit 330 may process and correlate patient data with certain therapeutic electrical signal parameters that were used within a pre-determined time period in which the patient data was acquired. For example, after the delivery of a particular therapeutic stimulation cycle, within a predetermined time period, various patient parameters may be collected by the IMD 200. This data may then be correlated and organized in such a fashion that trends relating to the relationship between patient data and various electrical signal parameters may be determined. Statistical and/or other types of data manipulation may also be performed by the data processing unit 330.

Further, the interface unit 280 may also comprise an input unit 340, which is capable of receiving data from the external unit 270 via the communication unit 260. Further, the interface unit 280 may also comprise an output unit 350, which is capable of driving data from the interface unit 280 to the external unit 270. The input unit 340 may comprise various registers, buffers and/or amplifiers to process and streamline data, e.g., convert data from serial to parallel, or vice versa. The output unit 350 is also capable of registering, buffering and/or amplifying data for transmission from the interface unit 280 to the external unit 270. The interface unit 280 is capable of receiving instructions and providing for various responsive actions in the IMD 200, as well as collecting, processing, and/or storing data. The interface unit 280 provides the ability for using a graphical user interface to provide interactivity between an external user e.g., a physician, and the IMD 200.

Figure 4:
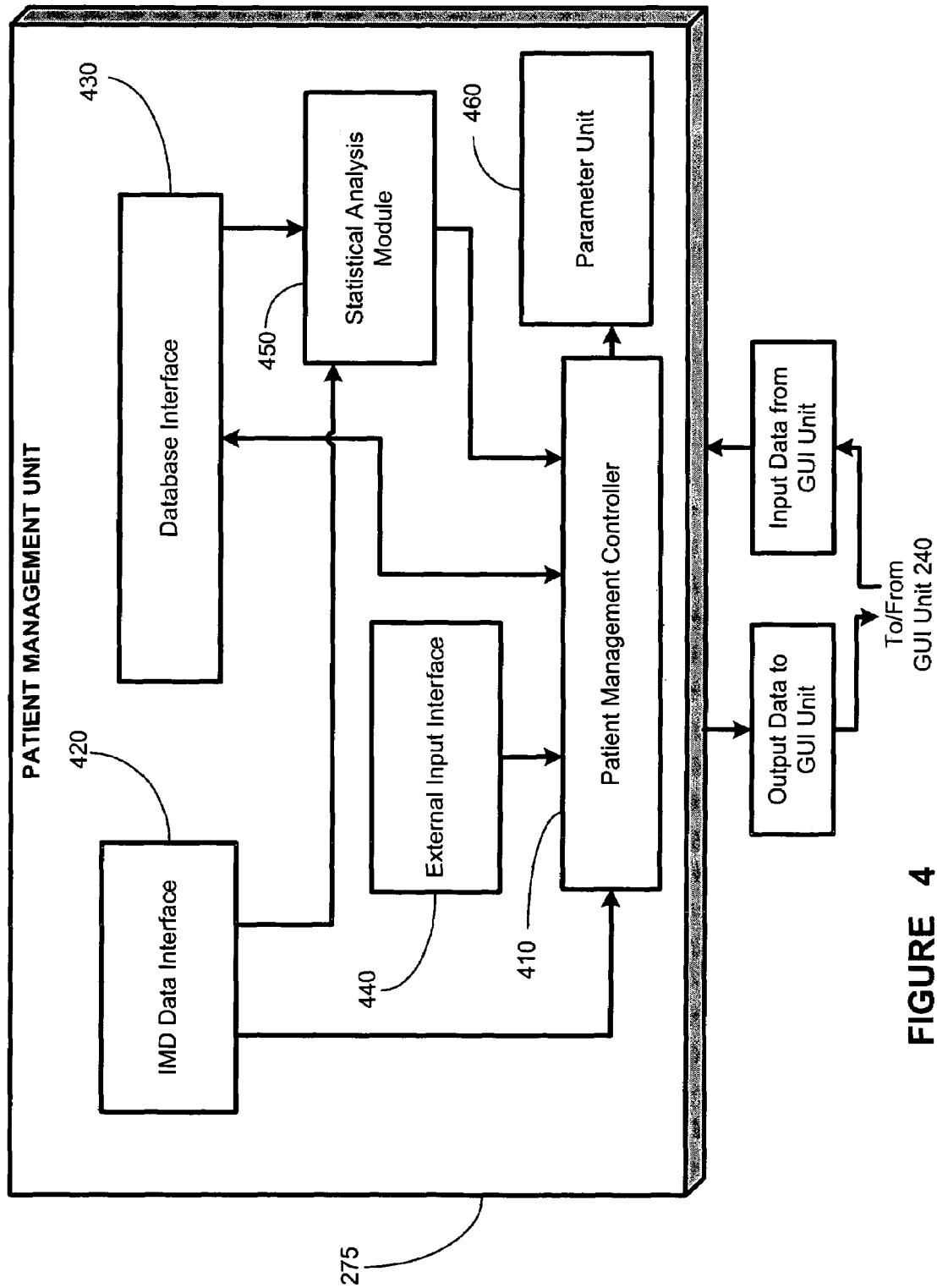
FIG. 4 is a more detailed block diagram depiction of a patient management unit of FIG. 2A or 2B, in accordance with one illustrative embodiment of the present invention.

FIG. 4 illustrates a more detailed block diagram depiction of the patient management unit 275 of external unit 270 (FIG. 2), in accordance with one illustrative embodiment of the present invention. The patient management unit 275 may include a patient management controller 410 that is capable of performing the various patient management tasks described herein. The patient management controller 410 may be a microprocessor, a firmware object (e.g., a field programmable gate array (FPGA) or an ASIC device), and/or a software module. The patient management controller 410 is capable of extracting data from the database unit 250 and/or local database unit 255 (FIG. 2) via a database interface 430. The database interface 430 may contain various amplifiers, buffers, registers and/or software modules to retrieve and/or send data from the database unit 250 and/or local database unit 255. The patient management unit 275 may also comprise an IMD data interface 420 that is capable of receiving from or sending data to the IMD 200. The IMD data interface 420 may comprise various amplifiers, buffers, registers and/or software modules to send data to the IMD 200 and/or receive data from the IMD 200. The patient management controller 410 may then provide data for display as part of a GUI unit 240, e.g., a graphical user interface. The patient management controller 410 may also receive data from the GUI unit 240 as input from an external user (e.g., a physician input).

The patient management unit 275 may also comprise an external input interface 440. The external input interface 440 is capable of receiving data from a user, e.g., a physician. Input from a user, via the external input interface 440, may prompt the patient management unit 275 to perform calculations for providing various recommended parameter settings for defining therapeutic electrical signals. The external input interface 440 may receive technical data relating to specific therapy parameters that are entered by a user/physician. For example, the particular charge required for a therapeutic electrical signal may be input by a physician and received by the external input interface 440. This information may then be used to perform further analysis to generate recommended therapy parameters. The user may accept the recommended therapy parameters, modify them, or input different therapy parameters. Based upon this input, the patient management unit 275 adjusts the therapy parameter settings in the IMD 200 for generating new therapeutic electrical signals.

The patient management unit 275 is capable of interrogating an IMD 200 in order to perform a statistical analysis of data resulting from treatments performed by one or more IMD 200. As a result of the interrogation performed by the patient management unit 275, the IMD data interface 420 and the database interface 430 may receive various external data sets that may be used to define the scope of the statistical analysis. The external data received may include therapy parameter settings used in previous therapeutic electrical signals, type of disease being treated, etc.

The patient management unit 275 may also comprise a statistical analysis module 450. The statistical analysis module 450 is capable of performing a statistical analysis of various types of data based upon the input received by the external input interface 440. The statistical analysis module 450 may, for example, recognize which particular type of disease (e.g., depression, epilepsy, etc.) is being treated. Further, various patient information and therapy goals may be provided by a user and received via the external input interface 440. Based upon the input from the user, the statistical analysis module 450 may provide statistical analysis of therapy parameters from which most patients are experiencing meaningful benefit. Based upon the data provided by the statistical analysis module 450, a parameter unit 460 in the patient management unit 275 may provide recommended parameter settings. For example, for treating a particular disease, data relating to a particular patient or a number of patients whose profiles are somewhat similar to those of the particular patient, may be statistically analyzed. The statistical analysis module may use patient parameter data obtained following the delivery of a therapeutic electrical signal, and may provide a statistical relationship between the characteristics of the therapeutic electrical signal (i.e., the therapy parameters) and the patient parameter(s) obtained after the application of the electrical signal. This process may be performed using data relating to a single patient and/or a group of patients. Based upon the statistical analysis, a suggested set of therapeutic parameter settings may be provided by a parameter unit 460. The user may accept the suggested therapy parameters or override them and modify one or more of their values. In this manner, a user may be guided or steered towards utilizing particular sets of therapy parameters that may have been determined to be more beneficial to a similar group of patients.

Further, the parameter unit 460 may also calculate various parameters based upon technical input from a user. For example, if a physician requires a particular charge per pulse to be delivered to a patient for treating a particular disease, the parameter unit 460 may provide various options to arrive at the particular charge per pulse. For example, a particular output current and pulse width that equates to the charge per pulse specified by the physician may be provided such that greater efficacy and/or superior improved performance of the IMD 200 may be achieved. For example, if the battery level of an IMD 200 is below a predetermined level, modification to the output current and pulse width of a particular therapy signal may be modified to generate longer battery usage efficiency while still delivering the charge per pulse specified by a physician. Similarly, the duty cycle of an electrical signal may be controlled based upon an input from a user, defining a particular duty cycle based on percentage of on-time versus off-time or total period of the stimulation signal. The patient management unit 275 may then provide various combinations of on-times and off-times that equate to a particular duty cycle. The user may then select one of the offered choices of duty cycle off/on combinations.

FIGS. 5-14 illustrate various screens (e.g., GUI displays) that may be displayed by the GUI unit 240 for performing various patient management functions, in accordance with one illustrative embodiment of the present invention. The screen displays in FIGS. 5-14 are exemplary interactive screens; however, those skilled in the art would appreciate that a variety of other screens may be used with the patient management embodiments provided herein and remain within the spirit and scope of the present invention. The GUI displays illustrated in FIGS. 5-14 may be integrated into a display device, a computer system, or a variety of types of electronic devices.

Figure 5:
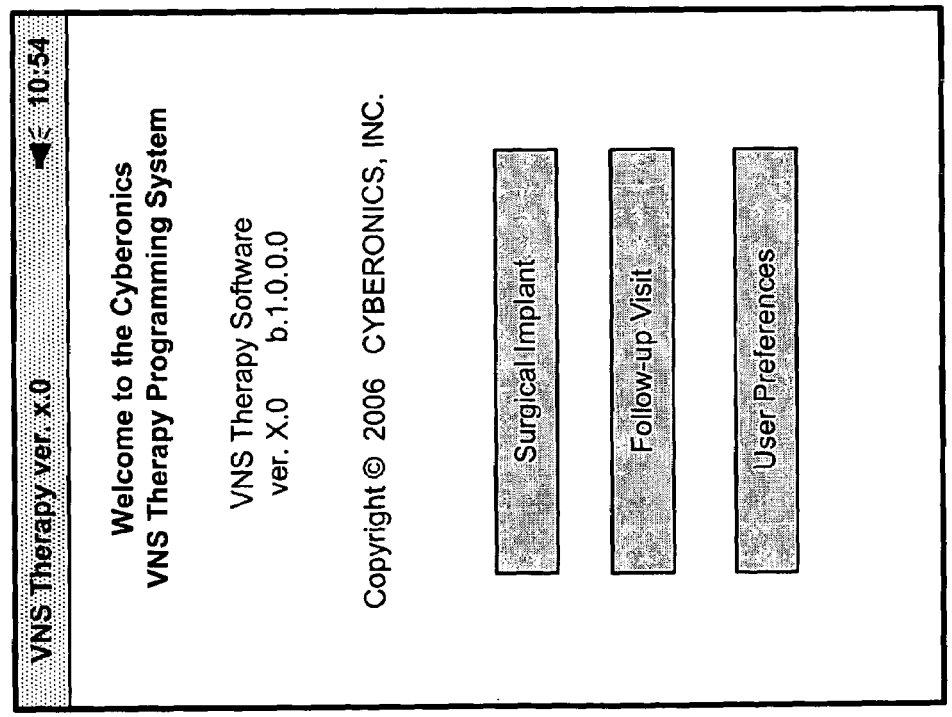

FIG. 5 illustrates a GUI screen that provides various information relating to the IMD 200 implanted in a particular patient's body, wherein the GUI screen may provide for interactive inputs. The screen illustrated in FIG. 5 provides a program patient data "screen" or GUI display, which illustrates various tasks that may be performed by the patient management system by embodiments of the present invention. The screen/GUI display of FIG. 5 illustrates the type of therapy software being employed, the version, etc. Further, one of several options may be selected to perform a particular task. For example, the GUI display of FIG. 5 provides for selecting a "Surgical Implant" process, a "Follow-up Visit" process, and a "User Preferences" process. Other processes may also be added to the display of FIG. 5 and remain within the sprit and scope of the present invention. As an example of the processes offered by the patient management unit 275, a user/physician may select the follow-up visit input to enter a "Follow-up Visit" mode of the patient management unit 275. For example, if the user selects the follow-up visit selection of FIG. 5, another screen (FIG. 6) may then be displayed by the patient management unit 275 that prompts and/or assists a user to interrogate the IMD 200.

Figure 6:
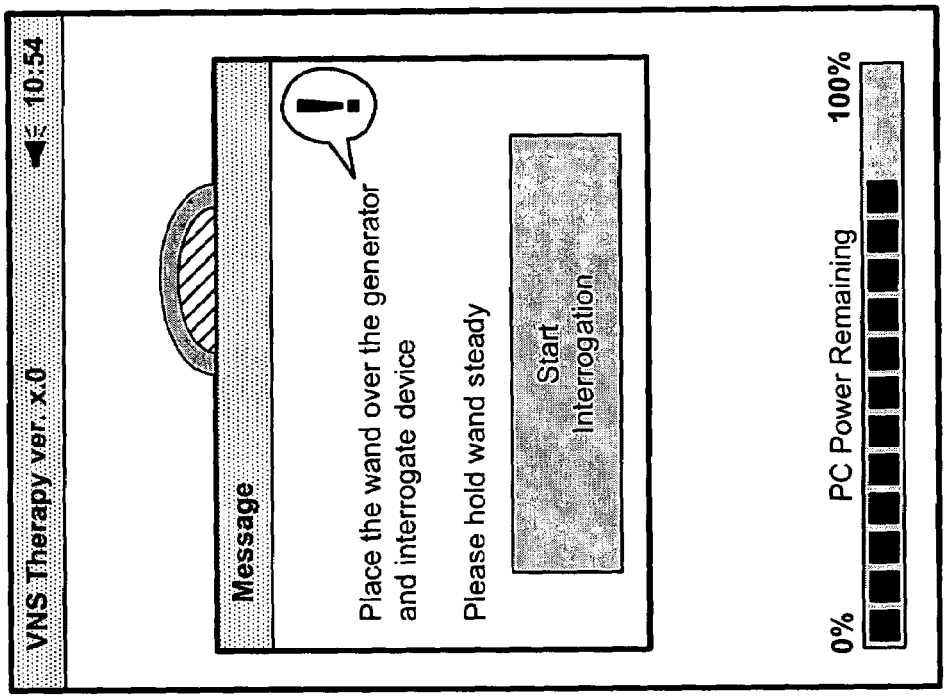
FIGS. 5-14 depict various screens (e.g., GUI displays) that may be displayed by the GUI unit of FIGS. 2A and 2B for performing various patient management functions, in accordance with one illustrative embodiment of the present invention.

FIG. 6 illustrates another exemplary screen that may be driven by the patient management unit 275 and displayed by the GUI unit 240 (FIGS. 2A, 2B). FIG. 6 illustrates a patient management screen that indicates a method for prompting a user to place a communication tool, such as the wand described above, proximate to the IMD 200 to interrogate the IMD 200. Upon properly locating the communication device in proximity to the IMD 200, a user may activate the "Start Interrogation" virtual button to perform an interrogation function. The interrogation process establishes communication between the IMD 200 and the external device 270 (FIGS. 2A, 2B) to receive various data inputs from the IMD 200.

Figure 7:
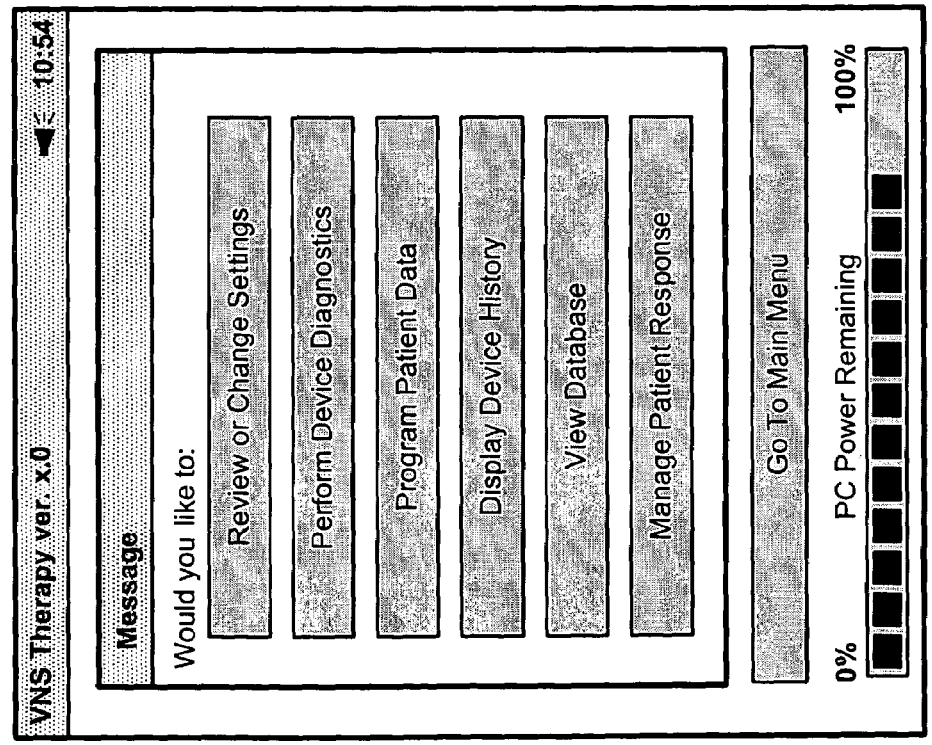

Upon performing the interrogation process described above, another GUI screen (FIG. 7) may be displayed by the patient management unit 275, wherein the GUI screen indicates various IMD settings. FIG. 7 illustrates another exemplary display that may be driven by the patient management unit 275 and displayed by the GUI unit 240 (FIGS. 2A, 2B). FIG. 7 illustrates a patient management screen that provides for a selection of various tasks, such as "Review or Change Settings," "Perform Device Diagnostics," "Program Patient Data," "Display Device History," "View Database," and/or other process type selection. Selection of any one of these options may activate various management/supervisory tasks that may be performed by the patient management unit 275. For example, if a user selects the "Review or Change Settings" selection, the patient management unit 275 may provide for entering a mode in which various therapy parameter settings may be reviewed and/or altered. For example, when the review or change settings options are selected by the user, another GUI screen (FIG. 8) may be displayed by the patient management unit 275.

Figure 8:
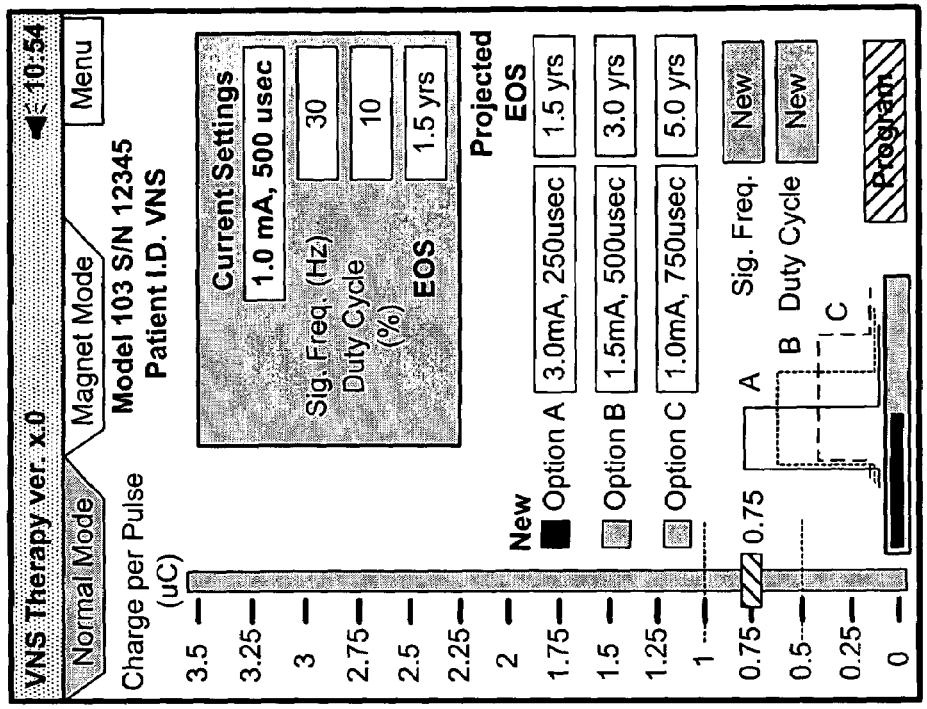

FIG. 8 illustrates another exemplary screen that may be driven by the patient management unit 275 and displayed by the GUI unit 240 (FIGS. 2A, 2B). FIG. 8 illustrates a patient management screen/display that indicates the model number and the patient ID. Further, an indication as to the charge per pulse setting for the electrical signal is also displayed. The interactive "slide-bar" button associated with the charge may be adjusted to modify the charge provided. The slide bar may be color coded to indicate recommended value ranges. Further, the current settings (i.e. those retrieved from the most recent interrogation) such as the output current, pulse width, signal frequency, and/or duty cycle percentages are also displayed. A projected end of service (EOS) of the IMD 200 may also displayed. The EOS may be an estimate that is based on current operating settings of the IMD 200. Persons of skill in the art will appreciate that less or greater information may be displayed than that shown in FIG. 8, and that different graphical displays of the data may also be used and remain within the spirit and scope of the present invention. For example, a series of "virtual buttons" may be used instead of the slide display shown in FIG. 8 for allowing the selection of a charge per pulse parameter.

FIG. 8 also illustrates three exemplary options that may be used based upon the selected charge per pulse. For example, a user may select to apply a charge per pulse of 0.75 micro-coulombs. This charge may be represented by various combinations of current and pulse-width parameters. For example, Option A may provide a 3 milliamp current pulse amplitude with a 250 microsecond pulse-width, Option B may provide for a 1.5 milliamp current pulse amplitude with a 500 microsecond pulse-width, and Option C may provide a 1.0 milliamp current pulse amplitude with a 750 microsecond pulse-width. All three options provide a 0.75 micro-coulombs charge per pulse. FIG. 8 also provides a display of the pulse shapes of the signal that would be provided by each of Option A, Option B and Option C signals. A user may select Option A, B, or C to provide a therapeutic electrical signal comprising the selected charge per pulse. Further, in one embodiment, a user may change various parameters in any of the options described herein.

FIG. 8 also illustrates that the projected EOS may be affected by the type of signal selected for a particular target charge per pulse of a therapy signal. For example, a charge per pulse of 0.75 micro-coulombs may be provided by various signals with varying pulse-width and amplitudes, such as the pulses associated with Options A, B, and C of FIG. 8. However, when a lower amplitude is used, in order to achieve the same charge value, a longer pulse width may be used. The use of a longer pulse width with a lower current amplitude may increase the length of service of the battery, which drives the operation of the IMD 200. For example, under Option A, a 3 milliamp current amplitude with a 250 microseconds pulse-width may result in a projected EOS of 1.5 years. In contrast, Option B, which calls for a 1.5 milliamp current amplitude and a 500 microsecond pulse-width may increase the EOS to 3 years. Further, the use of Option C calls for an even lower current amplitude of 1.0 milliamp, and a larger pulse-width i.e., 750 microseconds, to make up for the reduction of the amplitude to maintain a particular charge per pulse. This usage of low current amplitude may provide for an even longer EOS of 5 years. Therefore, the EOS may be extended based upon the adjustments described above, while still maintaining acceptable therapeutic efficacy. Although not explicitly displayed in the interest of clarity and ease of description, additional data, such as the signal on-time and off-time, may also be displayed in a similar GUI screen as the screen illustrated in FIG. 8. Additionally, the option to alter additional data displayed on a similar GUI screen may also be implemented and remain within the spirit and scope of the present invention.

Once a new charge per pulse setting and signal parameter options are selected in the GUI display of FIG. 8, all parameter combinations are updated and displayed as described above. In one embodiment, a default option may also be provided based upon prior experience and/or statistical analysis performed on a particular patient or a group of patients with similar circumstances. Further, the GUI display of FIG. 8 also provides for a selection of a signal frequency and a duty cycle, which is described in FIG. 10 and the accompanying description below.

Figure 9:
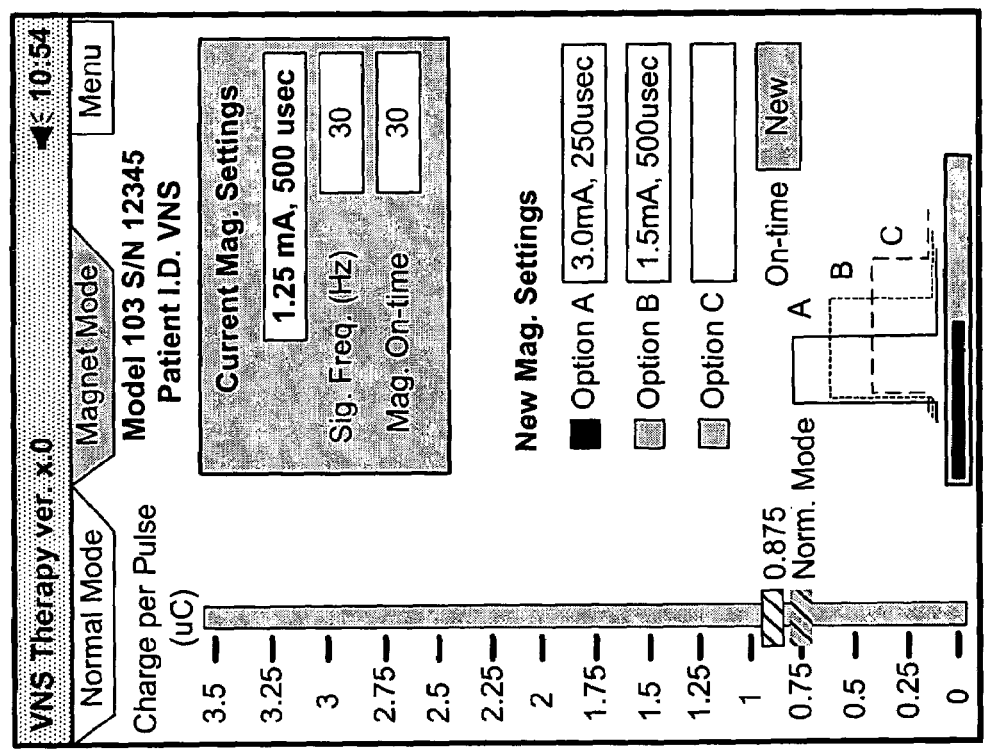

In some vagus nerve stimulation devices, particularly those for use in treating epilepsy, patients may be allowed to activate the device manually to abort or reduce the severity of an acute manifestation of the disease, e.g., an epileptic seizure. The patient may manually activate the device by placing a magnet on the skin beneath which the IMD 200 is implanted. This may activate an immediate therapeutic electrical signal that may different in its defining parameters than that for ordinary operation. This manual activation is referred to hereinafter as "Magnet Mode" operation. Ordinary operation according to a defined on-time and off-time is referred to herein as "Normal Mode" operation. Embodiments of the present invention allow a user to program parameters to define both Normal Mode and Magnet Mode therapeutic electrical signals. For illustrative purposes, the GUI display of FIG. 8 is depicted in a Normal Mode of operation. The GUI display of FIG. 8 may also be provided in a Magnet Mode, as illustrated in FIG. 9. Selecting the "Magnet Mode" would provide a user the capability of entering specific magnet mode electrical signal parameters, as described below.

Turning now to FIG. 9, another exemplary screen that may be driven by the patient management unit 275 and displayed by the GUI unit 240 (FIGS. 2A, 2B), is illustrated. FIG. 9 illustrates a Magnet Mode parameter GUI screen, which displays the current electrical signal parameters employed by the IMD 200 when the patient initiates a signal manually using a magnet. For example, the current magnet settings may be set at a charge per pulse of 0.87 micro-Coulombs based upon a 1.25 milliamp current amplitude with a 500 microsecond pulse width. The signal frequency and the magnet "on-time" (i.e., a component of duty cycle) are also displayed. Based upon the selection of the slide bar to select a particular charge per pulse, new magnet mode settings may be selected based upon various options provided to the user. For example, FIG.

9 illustrates an Option A that includes a 3.5 milliamps current amplitude with a 250 microsecond pulse width. Option B may provide for a 1.75 milliamps current amplitude and a 500 microsecond pulse width. Graphical depictions of the pulse shapes are also displayed in the GUI screen of FIG. 9. The GUI screen of FIG. 9 may also provide for adjusting the magnet mode on-time and off-time of a therapy signal.

Figure 10:
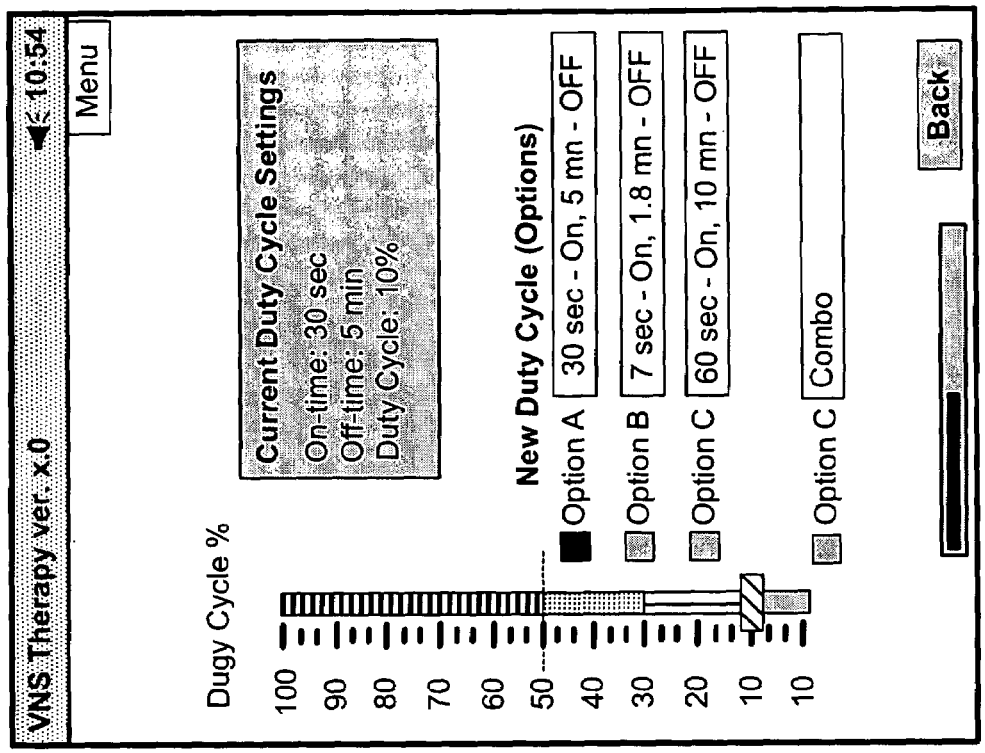

Referring back to FIG. 8, if the duty cycle option is selected in the GUI screen (by activating the "New" button adjacent to the "Duty Cycle" display on FIG. 8), a duty cycle screen as exemplified in FIG. 10, may be provided by the patient management unit 275. FIG. 10 illustrates an exemplary screen that may be driven by the patient management unit 275 and displayed by the GUI unit 240 (FIGS. 2A, 2B). FIG. 10 illustrates a patient management screen that indicates various settings relating to a duty cycle of a therapeutic stimulation signal. The duty cycle percentage may be selected by an interactive slide bar provided in the GUI screen of FIG. 10. The current duty cycle settings, such as the on-time, which is exemplified as 30 seconds, the off time, exemplified as five minutes, and the duty cycle percentage, exemplified as 10%, are illustrated. New duty cycle options may be provided based upon the selected duty cycle percentage. These options may also be based on statistical analysis of patient data, which may suggest that alternative duty cycle parameters should be selected. For example, for a duty cycle of 10%, Option A may provide for a 30 second on-time and a 5 minute off-time, wherein option B may call for a 7 second on-time and a 1.8 minute off-time and, Option C may provide for a 60 second on-time and a 10 minute off-time. Other options, such as a combination of various duty cycle options may also be provided as Option D. Further, in one embodiment, a user may change various parameters in any of the options described herein. Upon the selection of any of the options provided in the GUI screen of FIG. 10, a new duty cycle for the therapeutic electrical signal may be implemented. As described above, a default selection may be provided/recommended based upon statistical analysis that may suggest a desirable setting to provide for improved efficacy of the treatment provided by the IMD 200.

Figure 11:
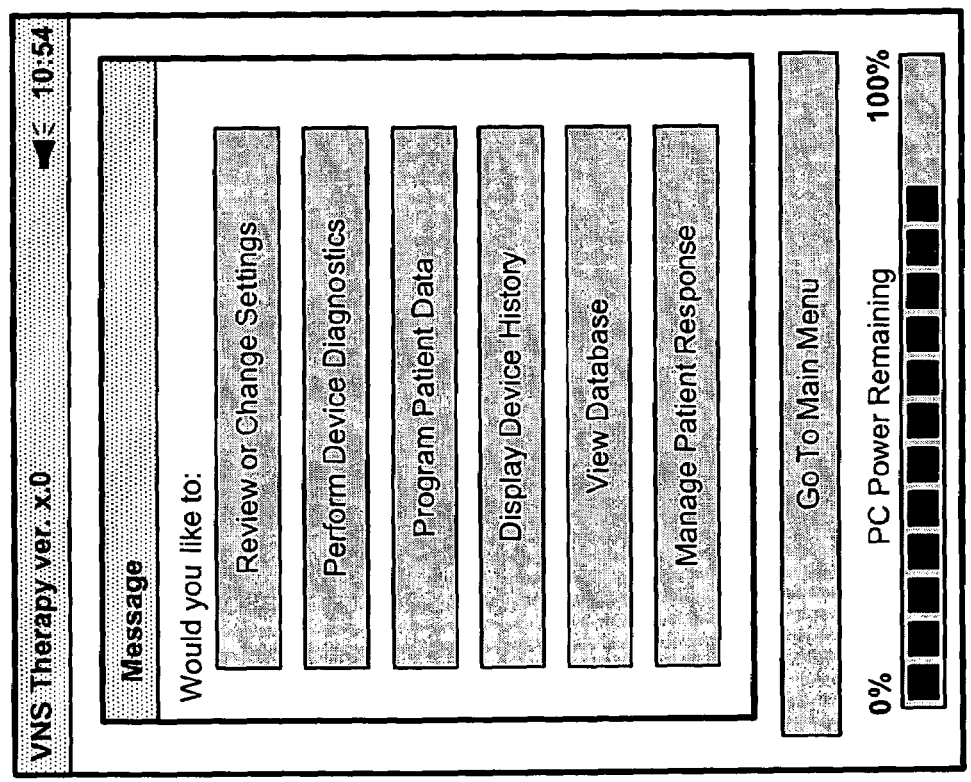

FIG. 10 also displays a menu selection (e.g., by a virtual button) that when depressed or activated, would provide the GUI screen illustrated in FIG. 11. The GUI display of FIG. 11, which corresponds to the display in FIG. 7, provides for the selection of various tasks that may be performed by the patient management unit 275. For example, the GUI screen of FIG. 11 provides a "View Database" selection option, which, in one embodiment, provides stored data without requiring an interrogation of the IMD 200. Based upon the "View Database" selection, a user may select various historical data-viewing options, such as parameter, diagnostics, and/or magnet histories. When the "View Database" selection is activated, a GUI screen providing various data-set selections for viewing historical data is illustrated in FIG. 12.

Figure 12:
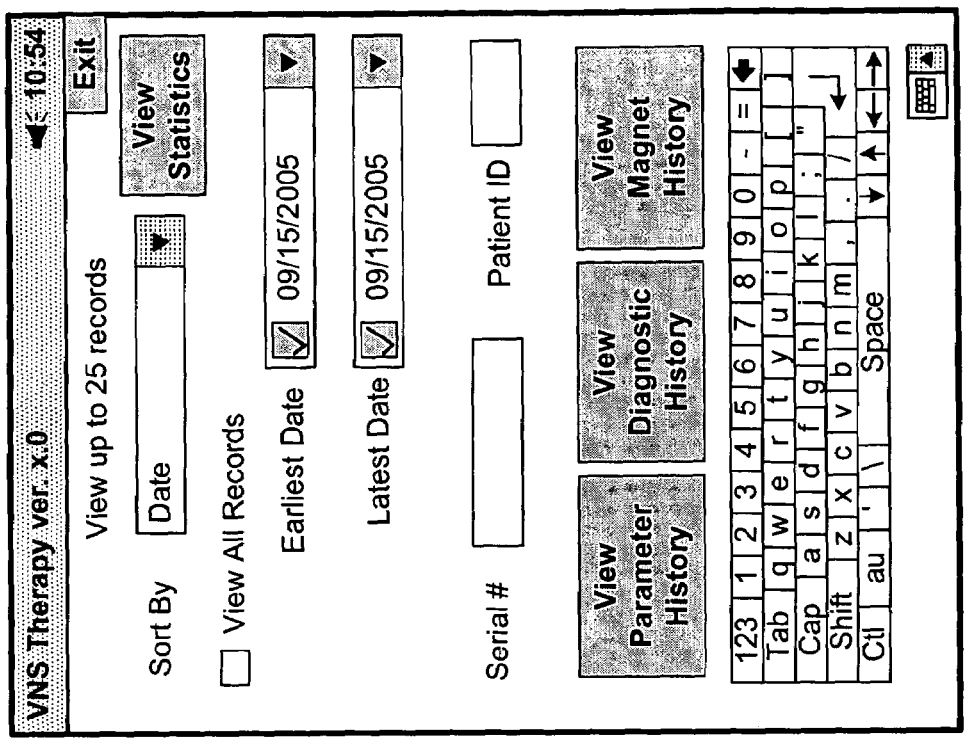

FIG. 12 illustrates another exemplary GUI screen that may be driven by the patient management unit 275 and displayed by the GUI unit 240 (FIGS. 2A, 2B). FIG. 12 illustrates a screen that provides the selection to view data. For example, data may be sorted by date range or other factors that may be selectable using a pull down menu. The earliest and latest dates to define a date range for organizing historical data may be selected. A virtual keyboard is provided in the GUI display of FIG. 12 to input the dates, serial numbers, patient identification numbers, etc. Several display options, such as "View Statistics," "View Parameter History," "View Diagnostic History" and "View Magnet History" options may be provided in the GUI display of FIG. 12. If, for example, a user selects the "View Statistics" option in FIG. 12, the patient management unit 275 may perform a statistical analysis of the selected set (e.g., selected by date range, indication, severity of disorder, patient age, patient gender, patient health, etc.) of data, which may be performed by the statistical analysis module 450 (FIG. 4). In the interest of clarity and ease of description, some examples of acquiring a selected set of data is implied by FIG. 12 but displayed date-range selection feature. However, based upon FIG. 12, those skilled in art would readily appreciate that in addition to the date-range selection of data, other selected sets of data may be acquired by the user, e.g., data selected by indication, severity of disorder, patient age, patient gender, patient health, etc. Upon selection of the "View Statistics" option of FIG. 12, various statistical analysis screens may be displayed.

Figure 13:
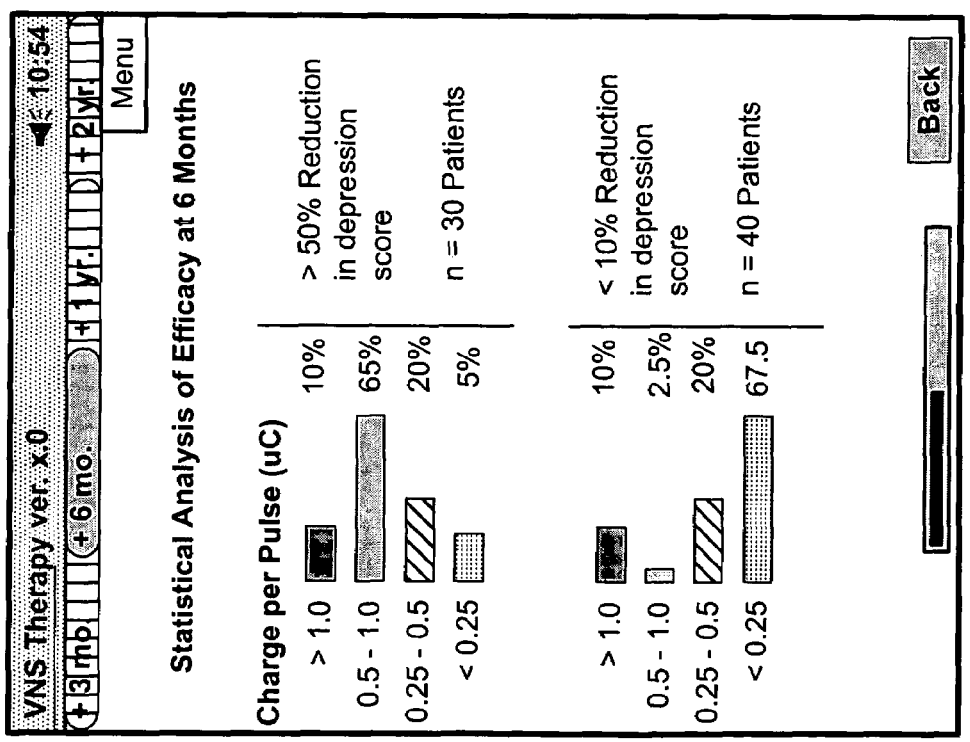

Turning now to FIG. 13, another exemplary screen of the statistics display provided by the patient management unit 275 may be displayed by the GUI unit 240 (FIGS. 2A, 2B). FIG. 13 illustrates a statistical analysis relating to the efficacy of the therapy at various time periods. For example, a three-month, a six-month, a one-year and/or a two-year period may be selected. In the example illustrated in FIG. 13, a six-month period of statistical analysis has been selected. Therefore, a six-month statistical analysis of efficacy is displayed in FIG. 13. This display includes statistical analysis of data available during the selected time period, wherein the data may be extracted from the database unit 250 and/or the local database unit 255 (FIGS. 2A, 2B).

The patient management unit 275 may use data stored in various databases (FIG. 2A, 2B) and/or patient management data that was entered at each office visit. The patient management unit 275 may correlate this data to the parameters to which the IMDs 200 were set during the time frames selected in FIG. 12. In the exemplary screen illustrated in FIG. 13, the depression treatment data indicates that 75% of all patients that had a greater than 50% reduction in depression ratings score were receiving an electrical signal having a charge per pulse in the range of 0.5 micro-Coulombs or greater. In this example, the depression treatment data of FIG. 13 illustrates that 67.5% of the patients that were having less than a 10% reduction in the depression score were receiving an electrical signal having a relatively low charge per pulse i.e., 0.25 micro-Coulombs. This information may suggest to a user that, at six months, most patients would react more positively to treatment at a higher charge per pulse than at a lower charge per pulse.

Figure 14:
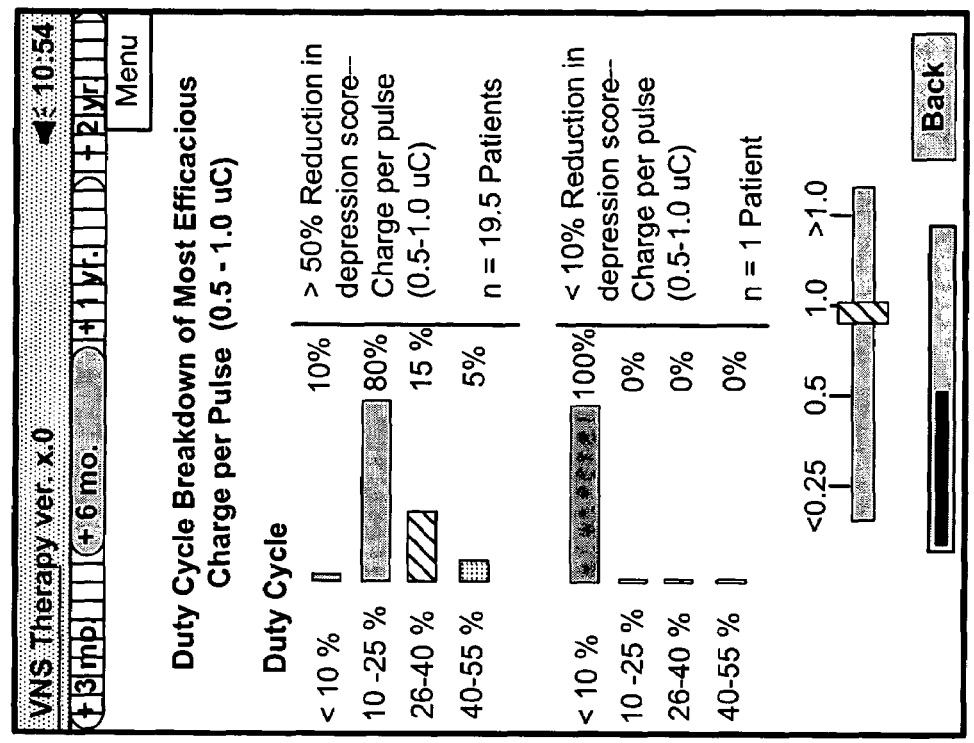

Turning now to FIG. 14, a more detailed exemplary breakdown of the data displayed in FIG. 13 in accordance with one embodiment of the present invention, is illustrated. The GUI screen of FIG. 14 may provide more details regarding a particular patient sub-population of FIG. 13. For example, in the GUI screen illustrated in FIG. 14, from the patients from whom data was collected and represented in FIG. 13, 80% received treatment that were defined by a duty cycle of approximately 10% to approximately 25%. Therefore, for a charge per pulse between 0.5 and 1.0 micro-coulombs, 80% of the patients achieved a greater than 50% reduction in depression score based upon a therapy signal characterized by a 10% to 25% duty cycle. Additionally, 15% of the patients receiving this level of improvement received therapy from a stimulation signal with a duty cycle range of 25% to 40%.

Using the example illustrated in FIGS. 13 and 14, for patients receiving less than a 10% reduction in depression score, a reasonable inference may be made that the reason why some of the patients who appear to receive an adequate level of the therapy signal may in fact not receive adequate treatment, is due to the variation of the duty cycle of the therapy signal. The exemplary statistical analysis results displayed in FIG. 13 indicates that, although 65 percent of the patients achieved a 60 percent reduction in depression score using a 0.5-1.0 micro-Coulomb charge per pulse signal, at least 2.5 percent of patients receiving a charge per pulse in this range experienced a reduction of depression score of less than 10 percent, signifying reduced efficacy compared to the larger group. FIG. 14 illustrates a further statistical breakdown of the patients receiving the most efficacious charge per pulse signal (i.e., the 0.5-1.0 micro-Coulomb signal). An examination of FIG. 14 reveals that a duty cycle of 10-25 percent provides a greater than 60 percent reduction in depression scores for 80 percent of the patients. Hence, a reasonable inference indicates that the efficacy of a therapy signal may depend not only on a dosage component (i.e., the charge per pulse) but also on a timing component (i.e., the duty cycle). Therefore, the relatively poor improvement in depression scores of some patients receiving the most effective charge per pulse (i.e., 0.5-1.0 micro-Coulomb) signal may be explained by the extremely low duty cycle (less than 10%) for the therapeutic electrical signal provided to the low-response patient group. This, in turn, suggests that the user may enhance efficacy for those patients by increasing the duty cycle. In the illustrative results provided in FIGS. 13 and 14, the most efficacious therapy signal comprises a dosage component of 0.5-1.0 micro-Coulomb charge per pulse, and a timing component of 10-25 percent duty cycle. Based upon the analysis of the exemplary data provided in FIGS. 13 and 14, an inference may be made that particular ranges of the duty cycle and the charge per pulse may be beneficial when treating a patient. Further, the accuracy of the analysis may be enhanced when additional patient data and therapy signal data are collected in the local and/or external databases (250, 255). FIGS. 13 and 14 display the user the total number of applicable patients as an 'n' value.

Figure 15:
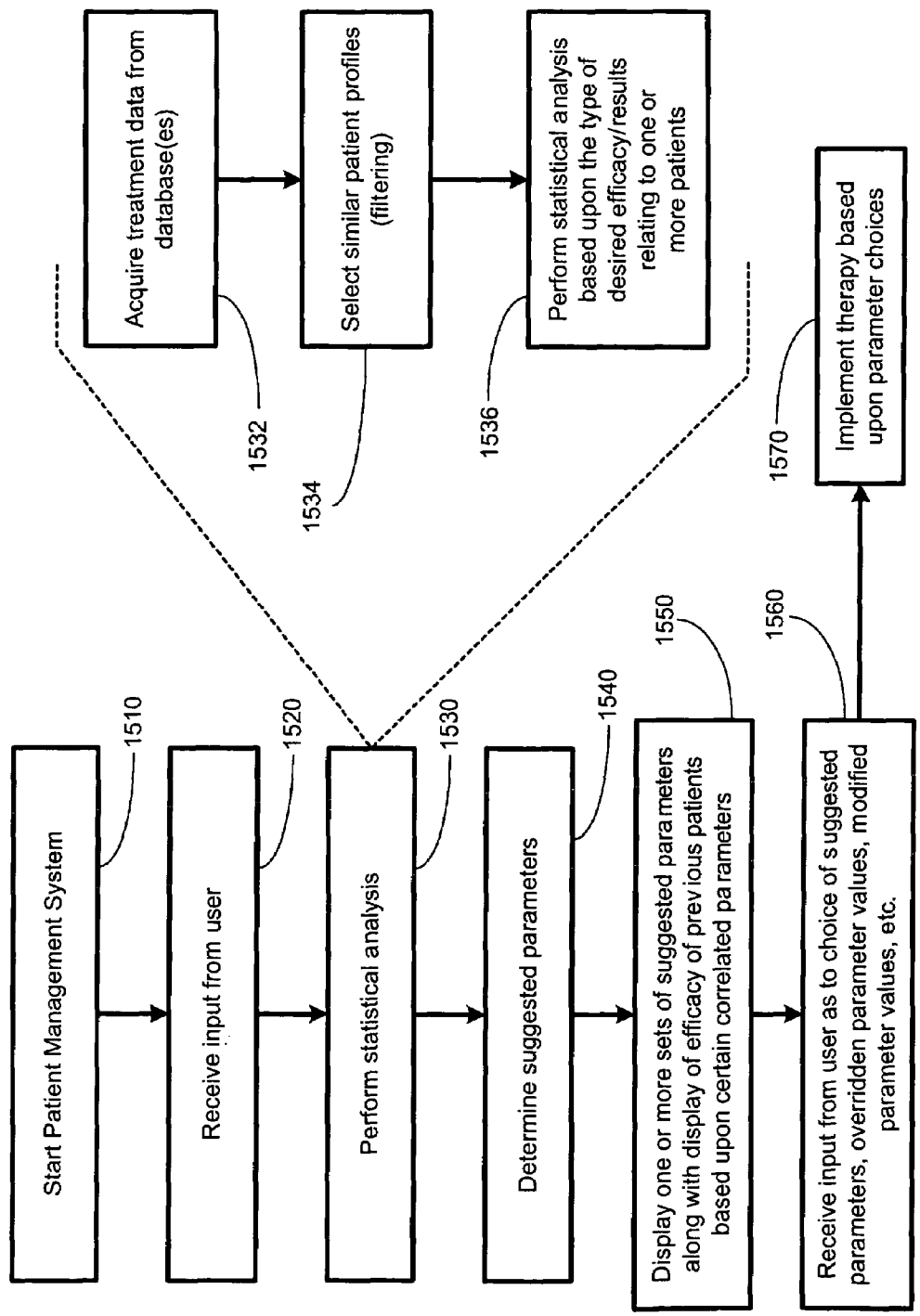
FIG. 15 is a flowchart of a method of performing the patient management function in accordance with one illustrative embodiment of the present invention.

Turning now to FIG. 15, a flow chart depiction of a method in accordance with an illustrative embodiment of the present invention is provided. The implementation of the patient management system may be initiated by activating the patient management unit 275 of the present invention (block 1510). Upon initiation of the patient management system, an instructive input may be received from the user (block 1520). This input may include various tasks to be performed by the patient management system and other information, such as patient information, the medical condition being treated, the therapy goals, and/or therapy parameter specifications.

Further, an analysis of certain patient data may also be requested by a user (e.g., a health care worker, a technician, a physician, etc.). Upon receiving the input, a statistical analysis may be performed by the patient management system using the input received. (block 1530). The statistical analysis may include steps, such as acquiring data from various databases (block 1532). Using this data, certain patient profiles are filtered out, while other patient profiles that are substantially similar are used to perform the statistical analysis. (block 1534). Based on this data, certain statistical analyses relating to the type of desired efficacy and/or treatment results in light of a patient's tolerance and/or other patient parameters are performed (block 1536). In other words, based upon the metes and bounds for the data analysis set by the user, an analysis may be performed in relation to the type of therapeutic results that are sought in light of a patient's particular characteristics by the use of a particular IMD 200. This process may provide the various screens described above, which may provide an indication as to the type of settings, e.g., duty cycle percentages, charge per pulse parameters, etc, that may improve treatment results. The steering or recommendations for directing improvements in therapeutic efficacy may be provided by displaying one or more suggested parameter values alongside the display of the efficacy of other patients in similar circumstances (block 1550). Utilizing this display, a user may accept, or reject and/or amend the various recommendations of therapy parameters provided above (block 1560). Based upon the parameters selected by the user, subsequent implementation of a new therapeutic electrical signal to treat a disease is performed (block 1570).

Utilizing embodiments of the present invention, various analyses using an external device, for example, may be performed on a patient during an office visit. The user may select an analysis based upon data relating to the patient and/or data relating to other patients, as to the effectiveness of certain therapeutic parameters and correlating them to patient parameters. Based upon this correlation, an indication is provided as to the effectiveness of certain types of therapy parameters. Embodiments of the present invention then provide for utilizing the various GUI screens to accept the suggested parameters, reject the suggested parameters and/or amend them to implement a new therapeutic electrical signal.

All of the methods and apparatuses disclosed and claimed herein may be made and executed without undue experimentation in light of the present disclosure. While the methods and apparatus of this invention have been described in terms of particular embodiments, it will be apparent to those skilled in the art that variations may be applied to the methods and apparatus and in the steps, or in the sequence of steps, of the method described herein without departing from the concept, spirit and scope of the invention, as defined by the appended claims. It should be especially apparent that the principles of the invention may be applied to selected cranial nerves other than or in addition to the vagus nerve to achieve particular results in treating patients having epilepsy.

The particular embodiments disclosed above are illustrative only as the invention may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the invention. Accordingly, the protection sought herein is as set forth in the claims below.

What is claimed:

1. A method for managing an electrical signal therapy provided by an implantable medical device, comprising:

applying a first electrical signal comprising a first therapy parameter to a vagus nerve of a patient using an implantable medical device that is implanted in the patient's body;

acquiring at least one patient parameter relating to an effect of applying said first electrical signal;

determining by a patient management unit a second therapy parameter for defining a second electrical signal to provide a therapy in response to said patient parameter, wherein said therapy comprises applying said second electrical signal comprising said second therapy parameter to said vagus nerve of said patient using said implantable medical device that is implanted in the patient's body;

displaying said second therapy parameter on an external device; and receiving an input signal selected from the group consisting of a signal indicative of the selection of said second therapy parameter and a signal indicative of not selecting said second therapy parameter.

2. The method of claim 1 wherein said signal indicative of not selecting said second therapy parameter comprises a signal providing a third therapy parameter to define said second electrical signal.

3. The method of claim 1, further comprising providing said second electrical signal to said vagus nerve of the patient body in response to receiving a signal indicative of the selection of said second therapy parameter.

4. The method of claim 1, wherein acquiring said patient parameter comprises acquiring data relating to an effect selected from the group consisting of a quality of life parameter, a seizure frequency parameter, a seizure characteristic parameter, a side effect parameter, a depression score parameter, and a brain-activity parameter.

5. The method of claim 4, wherein acquiring said quality of life parameter comprises acquiring data relating to an effect selected from the group consisting of a patient alertness parameter, a patient verbal skills parameter, a patient mood parameter, a patient achievement parameter, a patient memory parameter, an energy level parameter, a performance parameter, a concentration level parameter, an emotional parameter, a mental overview parameter, a coordination parameter, a balance parameter, a sleep parameter, and a sexual function level parameter.

6. The method of claim 4, wherein acquiring said seizure characteristic parameter comprises acquiring data selected from the group consisting of data relating to a generalized seizure experienced by the patient, a partial seizure experienced by the patient, a secondary generalized seizure experienced by the patient, and wherein acquiring said depression score parameter comprises acquiring data selected from the group consisting of data relating to a Psychological General Well-Being Scale (PGWB) test taken by the patient, the result of a WHO-Five Well-Being Index (WHO-5) test taken by the patient, the result of a Quality of Life in Depression Scale (QLDS) test taken by the patient, the result of a Social Functioning Scale-36 (SF-36) test taken by the patient; the result of a Social Functioning Scale-12 (SF-12) test taken by the patient, the result of a Quality of Life Enjoyment and Satisfaction Questionnaire-Short Form (Q-LES-Q-SF) test taken by the patient, and the result of a Streamlined Longitudinal Interval Continuation Evaluation-Condensed Version (SLICE-C) test taken by the patient.

7. The method of claim 6, wherein acquiring data relating to a generalized seizure experienced by the patient comprises acquiring data relating to a seizure experienced by the patient selected from the group consisting an absence seizure (petit mal), a Myoclonic seizure, a Clonic seizure, a Tonic-Clonic (grand-mal) seizure, an Atonic seizure (drop attacks), and wherein acquiring data relating to a partial seizure experienced by the patient comprises data acquiring relating to a seizure experienced by the patient selected from the group consisting of a Simple Partial seizure and a Complex Partial seizure.

8. The method of claim 1, wherein said first and second therapy parameters are selected from the group consisting of a current amplitude, a voltage amplitude, a rate of change of said current amplitude, a rate of change of said voltage amplitude, a time period of a rate of change of said current amplitude, a time period of a rate of change of said voltage amplitude, a pulse width, a rate of change of the pulse width, a time period of a rate of change of the pulse width, a frequency, a rate of change of the frequency, a time period of a rate of change of the frequency, a signal on-time, a signal off-time, and a duty cycle.

9. The method of claim 8, wherein determining said second therapy parameter for defining said second electrical signal to provide a therapy comprises:

correlating said at least one patient parameter with said first therapy parameter, wherein said correlating comprises establishing a relationship between at least one of a quality of life parameter, a seizure frequency parameter, a seizure characteristic parameter, a side effect parameter, a depression score parameter, and a brain-activity parameter, and at least one of a current amplitude, a voltage amplitude, a rate of change of the amplitude, a time period of a rate of change of the amplitude, a pulse width, a rate of change of the pulse width, a time period of a rate of change of the pulse width, a frequency, a rate of change of the frequency, a time period of a rate of change of the frequency, a signal on time, a signal off time, and a duty cycle of said first therapy parameter; and in response to said correlating step, calculating a different value of at least one of said current amplitude, a voltage amplitude, a rate of change of the amplitude, a time period of a rate of change of the amplitude, a pulse width, a rate of change of the pulse width, a time period of a rate of change of the pulse width, a frequency, a rate of change of the frequency, a time period of a rate of change of the frequency, a signal on time, a signal off time, and a duty cycle of said first therapy parameter as said second therapy parameter.

10. The method of claim 1, wherein receiving an input signal comprises providing a graphical user interface for allowing a user to input said input signal.

11. The method of claim 1, wherein displaying said second therapy parameter on an external device comprises displaying said therapy parameter on a computer selected from the group consisting of a hand-held computer system, a PC computer system, a laptop computer system, a server, a personal digital assistant (PDA), and an Apple-based computer system.

12. A method for managing an electrical signal therapy provided by an implantable medical device, comprising:

acquiring a plurality of values relating to at least one patient parameter following a first electrical signal applied to a cranial nerve of a patient to provide a therapy, wherein said first electrical signal comprises a first therapy parameter;

determining by a patient management unit an efficacy factor based upon said patient parameter, wherein determining said efficacy factor comprises analyzing a trend associated with said plurality of values relating to said at least one patient parameter;

determining a second therapy parameter to define a second electrical signal based upon said efficacy factor, wherein said therapy comprises applying said second electrical signal comprising said second therapy parameter to said cranial nerve of said patient using said implantable medical device that is implanted in the patient's body;

displaying said second therapy parameter; and receiving an input signal selected from the group consisting of a signal indicative of the selection of said second therapy parameter and a signal indicative of not selecting said second therapy parameter.

13. A method for managing an electrical signal therapy provided by an implantable medical device, comprising:

acquiring data indicative of a first patient parameter for a plurality of patients following the application of an electrical signal comprising a first therapy parameter to the vagus nerve of each patient of said plurality of patients;

determining by a patient management unit a statistical relationship between said data indicative of said first patient parameter and said first therapy parameter;

displaying said statistical relationship; and receiving an input signal for defining an electrical signal comprising a second therapy parameter for a patient based upon said statistical relationship.

14. A graphical user interface integrated into an external display device for managing a therapeutic electrical signal provided by an implantable medical device, comprising:

a first display region adapted to display a visual indication of a graphical representation of a second therapy parameter for defining a second electrical signal for application to a vagus nerve of a patient, said second therapy parameter being based upon a patient parameter relating to an effect of applying a first electrical signal comprising a first therapy parameter to a vagus nerve of a patient and determined by a patient management unit; and a second display region for receiving an input signal for defining said second electrical signal, said input signal selected from the group consisting of a signal indicative of the selection of said second therapy parameter and a signal indicative of not selecting said second therapy parameter.

15. The graphical user interface integrated into said external display device of claim 14, wherein said patient parameter comprises data relating to an effect selected from the group consisting of a quality of life parameter, a seizure frequency parameter, a seizure characteristic parameter, a side effect parameter, a depression score parameter, and a brain activity parameter.

16. The graphical user interface integrated into said external display device of claim 15, wherein said quality of life parameter comprises data relating to an effect selected from the group consisting of a patient alertness parameter, a patient verbal skills parameter, a patient mood parameter, a patient achievement parameter, a patient memory parameter, an energy level parameter, a performance parameter, a concentration level parameter, an emotional parameter, a mental overview parameter, the coordination parameter, a balance parameter, the amount of sleep parameter, and a sexual function level parameter.

17. The graphical user interface integrated into said external display device of claim 15, wherein said seizure characteristic parameter comprises data selected from the group consisting of data relating to a generalized seizure experienced by the patient, a partial seizure experienced by the patient, a secondary generalized seizure experienced by the patient, and said depression score parameter comprises data selected from the group consisting of a Psychological General Well-Being Scale (PGWB) test taken by the patient, the result of a WHO-Five Well-Being Index (WHO-5) test taken by the patient, the result of a Quality of Life in Depression Scale (QLDS) test taken by the patient, the result of a Social Functioning Scale-36 (SF-36) test taken by the patient; the result of a Social Functioning Scale-12 (SF-12) test taken by the patient, the result of a Quality of Life Enjoyment and Satisfaction Questionnaire-Short Form (Q-LES-Q-SF) test taken by the patient, and the result of a Streamlined Longitudinal Interval Continuation Evaluation-Condensed Version (SLICEC) test taken by the patient.

18. The graphical user interface integrated into said external display device of claim 17, wherein data relating to a generalized seizure experienced by the patient comprises data relating to a seizure experienced by the patient selected from the group consisting an absence seizure (petit mal), a Myoclonic seizure, a Clonic seizure, a Tonic-Clonic (grand-mal) seizure, an Atonic seizure (drop attacks), and wherein acquiring data relating, to a partial seizure experienced by the patient comprises data relating to a seizure experienced by the patient selected from the group consisting of a Simple Partial seizure and a Complex Partial seizure.

19. The graphical user interface integrated into said external display device of claim 14, wherein said first and second therapy parameters are selected from the group consisting of a current amplitude, a voltage amplitude, a rate of change of said current amplitude, a rate of change of said voltage amplitude, a time period of a rate of change of said current amplitude, a time period of a rate of change of said voltage amplitude, a pulse width, a rate of change of the pulse width, a time period of a rate of change of the pulse width, a frequency, a rate of change of the frequency, a time period of a rate of change of the frequency, a signal on-time, a signal off-time, and a duty cycle.

20. The graphical user interface integrated into said external display device of claim 19, wherein said second therapy parameter for defining said second electrical signal comprises data relating to a correlation of said at least one patient parameter with said first therapy parameter.

21. The graphical user interface integrated into said external display device of claim 20, wherein said graphical user interface comprises a third display region for allowing a user to input said input signal.

22. The graphical user interface integrated into said external display device of claim 14, wherein said graphical user interface is provided on at least one of a hand-held computer system, a PC computer system, a laptop computer system, a server, a personal digital assistant (PDA), and an Apple-based computer system.

23. A computer readable program storage device encoded with instructions that, when executed by a computer, performs a method for managing an electrical signal therapy provided by an implantable medical device, comprising:

applying a first electrical signal comprising a first therapy parameter to a cranial nerve of a patient;

acquiring at least one patient parameter relating to an effect of applying said first electrical signal;

determining a second therapy parameter for defining a second electrical signal to provide a therapy in response to said patient parameter, wherein said therapy comprises applying said second electrical signal comprising said second therapy parameter to said cranial nerve of said patient using said implantable medical device that is implanted in the patient's body;

displaying said second therapy parameter on an external device; and receiving an input signal selected from the group consisting of a signal indicative of the selection of said second therapy parameter and a signal indicative of not selecting said second therapy parameter.

* * * * *